(12) United States Patent
Kelsch et al.

(10) Patent No.: US 7,890,192 B1
(45) Date of Patent: Feb. 15, 2011

(54) METHOD FOR INSERTING A LEAD ELECTRODE INTO BODY TISSUE USING A ROTATABLE LEAD INTRODUCER

(75) Inventors: Daniel N. Kelsch, Fairview, OH (US); James L. Mellor, St. Paul, MN (US); Kenneth P. Rundle, Independence, OH (US); Roger B. Fell, Avon Lake, OH (US); Scott E. Jahns, Hudson, WI (US); Dave S. Erickson, Stillwater, MN (US); Vincent A. Fischer, III, Minneapolis, MN (US); Kent D. Anderson, Champlin, MN (US)

(73) Assignee: Greatbatch Ltd., Clarence, NY (US)

( * ) Notice: Subject to any disclaimer, the term of this patent is extended or adjusted under 35 U.S.C. 154(b) by 152 days.

(21) Appl. No.: 12/478,797

(22) Filed: Jun. 5, 2009

Related U.S. Application Data

(62) Division of application No. 10/840,668, filed on May 6, 2004, now Pat. No. 7,544,197.

(60) Provisional application No. 60/468,352, filed on May 6, 2003.

(51) Int. Cl.
*A61B 19/00* (2006.01)
*A61N 1/00* (2006.01)

(52) U.S. Cl. .................. 607/130; 607/131; 600/375; 606/129

(58) Field of Classification Search .......... 607/126, 607/127, 130, 131; 600/375, 377; 606/129; 464/106; 81/177.7–177.75
See application file for complete search history.

(56) References Cited

U.S. PATENT DOCUMENTS 2,775,912 A   1/1957   Skage 3,890,859 A   6/1975   Grabovac et al.
4,552,150 A   11/1985  Zacouto (Continued)

FOREIGN PATENT DOCUMENTS

EP   1189539 B1   9/2003

(Continued)

OTHER PUBLICATIONS

Roelke et al., Serial Lead Impedance Measurements Confirm Fixation of Helical Screw Electrodes During Pacemaker Implantation, PACE, Apr. 2000, Pt. 1 pp. 488-492, vol. 23.

*Primary Examiner*—Mark W Bockelman
(74) *Attorney, Agent, or Firm*—Michael F. Scalise

(57) ABSTRACT

A method for inserting a lead electrode into body tissue using a rotatable lead introducer is described. The introducer can include a distal element for releasably engaging a lead head controllable from a proximal control located outside of the body. An inner stem can extend between a proximal portion and a distal portion, and be pivotally and rotatably coupled to the distal lead engagement mechanism. An outer tube can be rotatably disposed over the inner stem and be flexibly coupled over the pivot to rotationally drive the distal element. A helical epicardial-myocardial lead electrode can be secured and oriented straight ahead and introduced through a port or small incision with the introducer in a straight configuration. The introducer can then be bent and rotated to screw the helical electrode into the heart.

23 Claims, 21 Drawing Sheets

U.S. PATENT DOCUMENTS

| | | |
|---|---|---|
| 5,549,637 A | 8/1996 | Crainich |
| 5,814,088 A | 9/1998 | Paul et al. |
| 7,092,765 B2 | 8/2006 | Geske et al. |
| 7,328,071 B1 | 2/2008 | Stehr et al. |

FOREIGN PATENT DOCUMENTS

| | | |
|---|---|---|
| WO | 2004026393 A2 | 4/2004 |

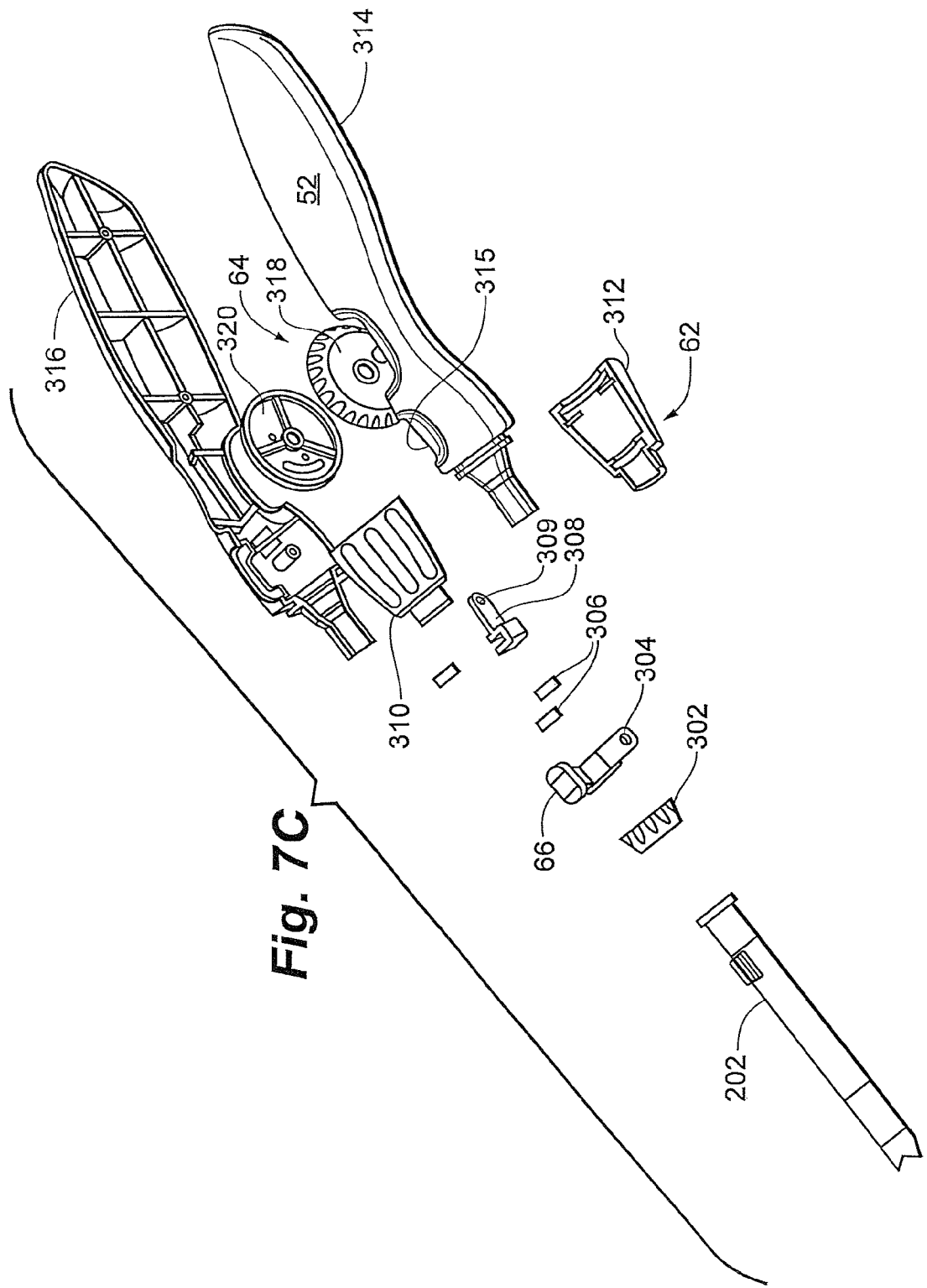

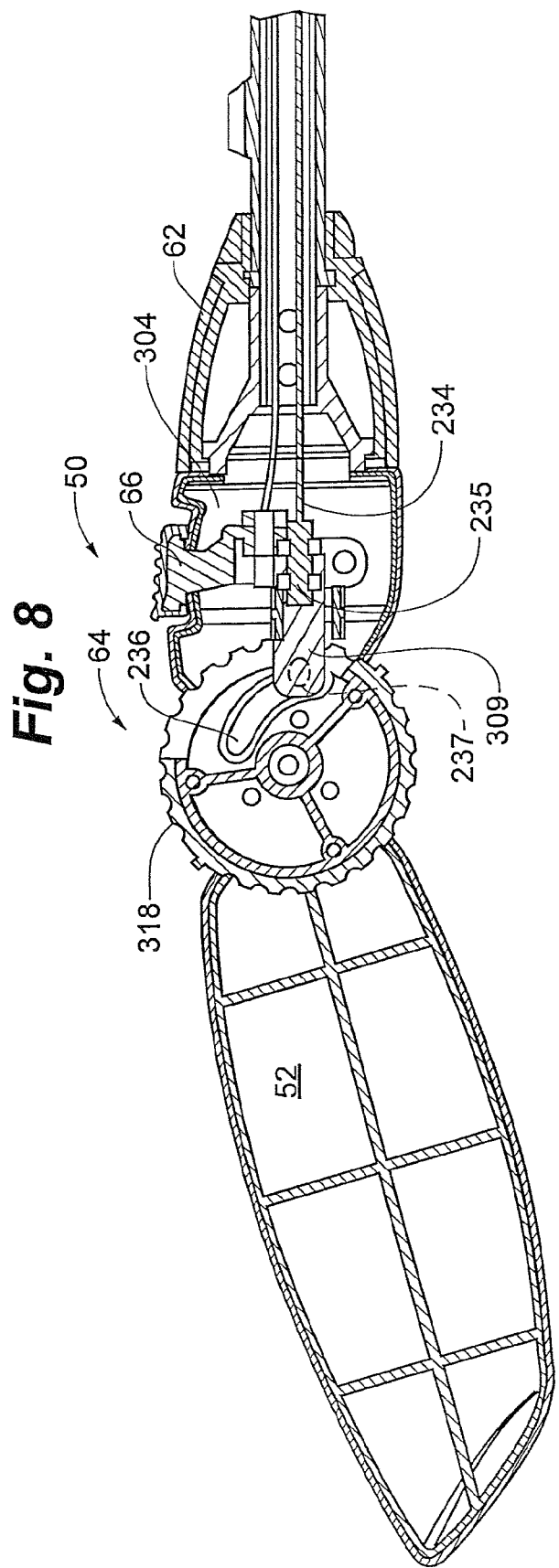

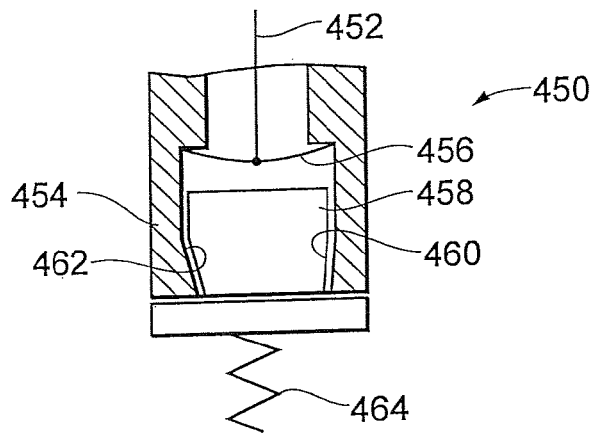
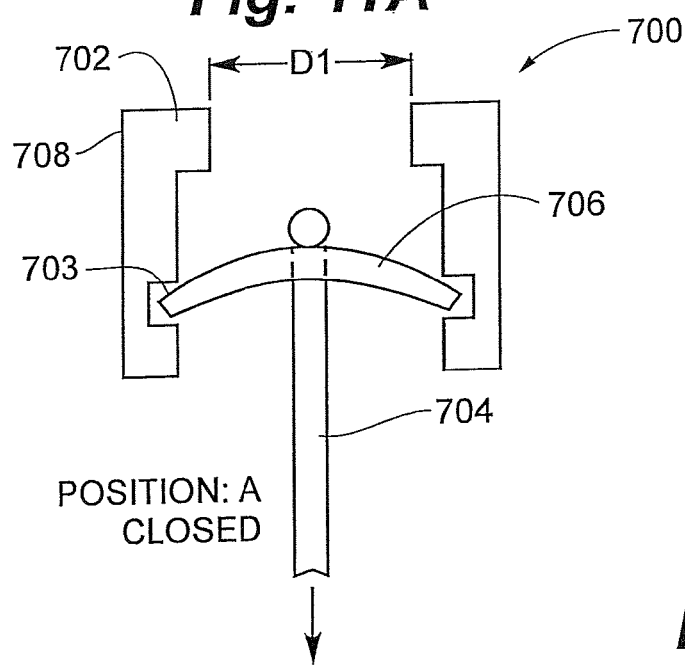
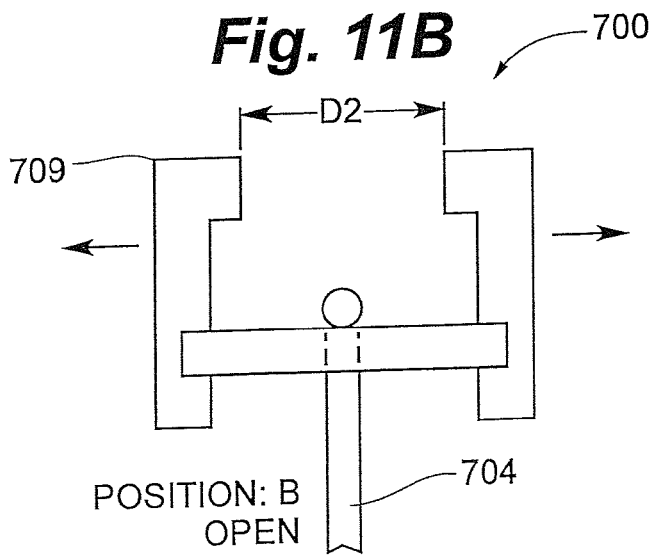

METHOD FOR INSERTING A LEAD ELECTRODE INTO BODY TISSUE USING A ROTATABLE LEAD INTRODUCER

CROSS-REFERENCE TO RELATED APPLICATIONS

The present application is a divisional of U.S. patent application Ser. No. 10/840,668, filed May 6, 2004, now U.S. Pat. No. 7,544,197, which claims priority from U.S. Provisional Patent Application Ser. No. 60/468,352, filed May 6, 2003.

FIELD OF THE INVENTION

The present invention is related generally to medical devices. More specifically, the present invention is related to minimally invasive medical instruments for securing devices within the human body. One example of use is securing an epicardial-myocardial pacing lead to the heart.

BACKGROUND OF THE INVENTION

Several major CRM companies have developed special pacemakers "IPGs" that allow for the delivery of resynchronization therapy. This technology uses atrial synchronized, biventricular pacing and requires placement of a lead in or on the right atrium as well as the right and left ventricles. Placement of a lead inside the left ventricle has not been clinically feasible to date due to dislodgement and the risk of embolism formation potentially leading to a stroke.

To answer the challenge of placing the left ventricle (LV) lead, considerable effort has gone into the development of special leads and delivery systems for placing the LV lead in a coronary vein. These leads are often referred to as coronary sinus (CS) leads, since the lead passes through the CS. CS leads have been challenging for the electrophysiologist to place and often require considerably more time and increased fluoroscopy exposure than traditional endovascular right side leads. Following implantation, the CS lead may dislodge in 10+% of patients leading to less than desirable performance. At least 10% of the target patients are not candidates for CS leads due to the anatomical structure of their coronary veins.

An alternative to CS leads is the use of epicardial or myocardial leads. Traditionally, these leads have been placed during open chest surgical procedures (sternotomy) or through a less traumatic subxiphiod or subcostal approach to the apex of the heart. The invasiveness of a full sternotomy would not be well tolerated by the CHF patients.

The placement of the lead on the apex of the heart is not desirable for resynchronization therapy. It is generally believed that the target location on the heart for resynchronization therapy is the lateral side of LV 2-3 cm apical of obtuse marginal and circumflex artery junction. Optimization of the target site may be achieved by ECG mapping of the heart to determine the location on the left ventricle that has the latest activation. Other epicardial locations that are normally accessible only with a sternotomy may be reached through the use of some embodiments the present invention in minimally invasive (MI) approaches.

To reach the target location through MI techniques, endoscopic ports and special endoscopic instruments may be employed. During a minimally invasive procedure it may be desirable to pass the device through a port. The port ID and length limit the amount of curvature that can preexist in an implant tool.

It is desirable for a lead to be implanted with the center axis of the helical electrode normal to the surface of the heart. The rigid prior art introducers often require a straight line between the point of entering the body and the implant position on the heart. This alignment is extremely challenging since the target spot is not directly visualized. Many or most traditional lead introducers are not suited for a MI approach due to their size and need for a straight-line approach. When leads must be placed on the superior portion of the left ventricle, as with resynchronization therapy, specialized tools and methods must be employed to reduce trauma to the patient and reach the appropriate location.

What would be desirable are devices and methods for placing epicardial-myocardial leads using minimally invasive techniques.

SUMMARY OF THE INVENTION

The present invention includes a device for rotating and inserting an epicardial-myocardial lead including a helical electrode, an electrode head, and a lead body. The device can include means for releasably engaging the electrode head disposed in the device distal portion and means for controlling the releasable engaging means from the device proximal portion. The device can further include means for controllably bending the device distal portion and means for controlling the controllable bending from the device distal portion. Devices can also include means for controllably rotating the releasable engaging means, and means for controlling the controllable rotating means from the device proximal portion.

Devices according to the present invention can be described in terms of three types of motions. The first type of motion is a bending or steering motion that can transform an introducer tool from a substantially straight configuration to a configuration having the distal portion bent to an orientation that may be perpendicular to the straight body of the introducer, to present the introducer distal end normal to the heart or other organ surface. Bringing the distal end normal to the heart surface can also present the helical electrode normal to the heart surface. The bending motion can be accomplished by many mechanisms. In one device, an inner stem or stiffening element can have a distal pivot point for allowing a distal element to pivot between the straight ahead and perpendicular positions. The bending movement can be controlled by a push-pull rod forming a lever arm with the pivot point in some embodiments. The controllable bending of the present invention may be accomplished while the bendable portion is disposed within a patient, inserted through an incision or port. This may be contrasted with manually or otherwise bending a malleable shaft followed by inserting the bent shaft into the patient.

A second type of movement exhibited by devices according to the present invention is a release movement. The epicardial-myocardial lead typically has a lead head coupled to a lead body carrying a conductor, and a helical electrode also coupled to the lead head for penetrating into the epicardium and myocardium. The release mechanism can grasp the lead head firmly in a first configuration and release the lead head in a second configuration. Some devices have an externally grasping collet mechanism for grasping the outside of the lead head until release. The collet can release the lead head by transversely or radially moving the collet jaws outward. Other release mechanisms can be used with lead heads having a head cavity having outer walls. In these mechanisms, a transversely movable release element can be transversely or radially moved inward, to release the pressure on the inner walls of the lead head cavity, thereby releasing the lead head from the delivering device. In some devices, the release mechanism is actuated by a pull wire or cable.

A third type of movement found in the present invention is a rotation or torque movement for rotating the helical electrode into the myocardial tissue. This rotation can be performed through multiple turns. The rotation can be supplied by the operator rotating a proximal control knob. The rotation is preferably delivered through an external, rotating outer tube that can be disposed over the inner stem. The torque can be transmitted over the bendable portion using a drive spring, helical coil, or other similar flexible sleeve that is capable of transmitting torque. The outer tube and coil functions may be served by a single integral outer tube or coil in some embodiments. The drive spring or other coupling can be coupled at its distal end to a portion of the introducer that is free to rotate and that is coupled to the electrode head. In some devices, a distal element is pivotally coupled at a proximal region to the inner stem, and has a distal element distal region that is free to rotate relative to the portion coupled to the pivot. In some devices, the pivot for bending is coupled to an inner portion of the distal element and the outer portion of the distal element is free to rotate. In still other devices, a hollow universal joint is employed to accomplish the combined pivoting and rotating motions.

Any suitable mechanism for rotatably and pivotally coupling the lead head engaging mechanism to the main shaft or stem of the device is within the scope of the invention.

The adjustable angle used in the present invention allows for numerous real time adjustments when approaching the heart. Some devices according to the present invention include one remotely steerable surgical tool with a single hinge point that is capable of a maximum range of motion of approximately 95°. It can consist of an internal hinged "skeleton" that can be used to support steering and an external tube structure that is used to transmit torque to the helical fixation device on the lead. Some embodiments of the invention allow for single-handed operation by the implanter.

The present invention also includes lead management features, including mechanisms for releasably securing a lead body along the rotating outer tube of the introducer device. Some devices according to the present invention include a friction safety clutch for limiting the rotational torque delivered to the helical electrode. Some devices further include impedance measuring circuitry for measuring the impedance across the bi-polar electrode while the electrode is being rotated and inserted into the myocardial tissue.

The present invention provides a surgical tool that can be used for implantation of epicardial-myocardial cardiac pacing leads that require rotation for fixation. The tool can also be used for implanting other types of stimulation leads that require multiple turns for fixation; these applications may include gastrological stimulation leads for reflux disorders or for appetite suppression.

BRIEF DESCRIPTION OF THE DRAWINGS

FIG. 7C is an exploded view of the handle region of the lead introducer of FIG. 1 including the release lever for actuating the pull wire, the knob for rotating the outer tube, and the wheel for actuating the push-pull rod to bend the hinge;

FIG. 8 is a fragmentary, side, cutaway view of the handle mechanism of FIG. 7C;

FIG. 10 is a fragmentary, highly diagrammatic, transverse cross-sectional view of a collet mechanism having an undercut distal jaw region for mechanically engaging a lead head;

FIGS. 11A and 11B are fragmentary, highly diagrammatic views of a Bellville washer or clover spring mechanism for expanding the jaws of a collet when the pull cable is retracted, to release the lead head;

DETAILED DESCRIPTION

Figure 1:
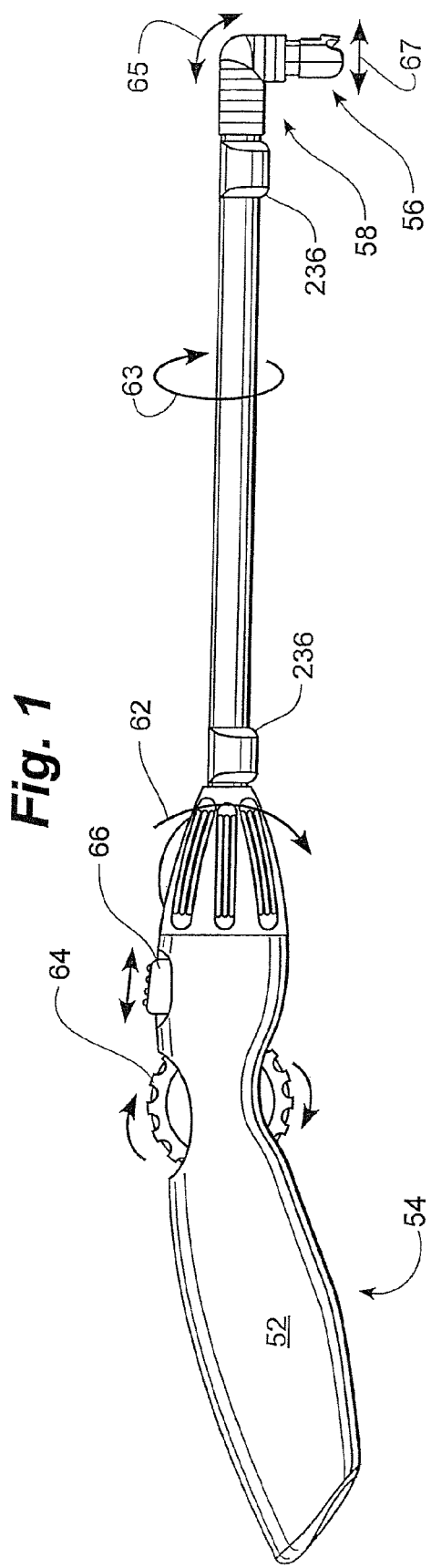
FIG. 1 is a perspective view of a lead introducer having a proximal steering or bending knob, a lead head rotation or torque control knob, a lead release lever, a bendable distal portion, and a distal lead head engagement portion.

FIG. 1 illustrates a lead introducer 50 including a handle 52, a proximal portion 54, a distal portion 56, and a bendable portion 58. Introducer 50 further includes a rotation/torque knob or control 62, a steering or bending knob or control 64, and a release slider control 66. Knob 64 can be rotated to effect bending movement indicated at 65. Control 66 can be slid to effect head release indicated at 67. Knob 62 can be rotated to effect outer tube and collet rotation indicated at 63. Lead guides 236 may allow the lead to be rotatably carried with the rotating outer tube. The various elements introduced in FIG. 1 will be described in detail elsewhere.

Figure 2A:
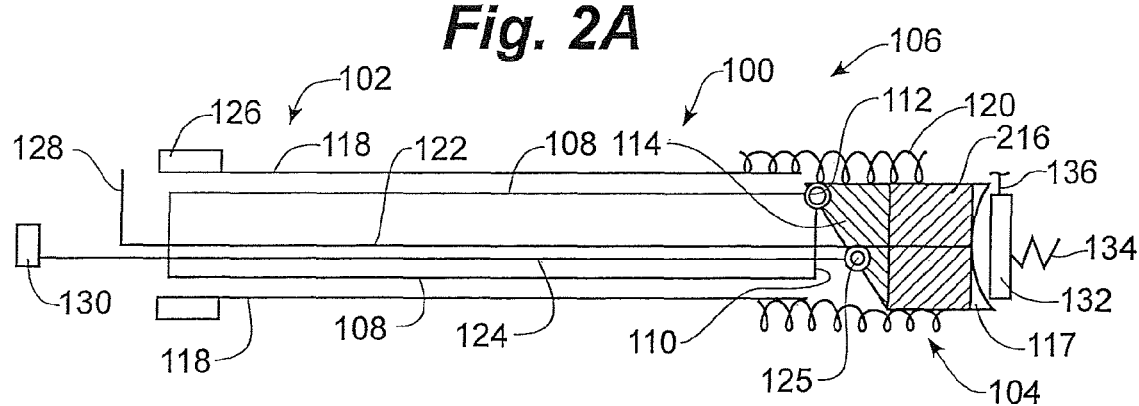
FIG. 2A is a highly diagrammatic, side view of a lead introducer having a rotatable outer main tube, a fixed inner stem, a lead release pull wire, a push/pull steering rod, a distal lead engagement mechanism, a lead head, and a drive coupling disposed over the distal bend.

FIG. 2A illustrates a highly diagrammatic lead introducer 100 including a proximal portion 102, a distal portion 104, and a bendable portion 106. Lead introducer 100 includes an inner stem or stiffener 108 which may be a solid shaft or tube that does not rotate and may be fixedly secured to the handle in some embodiments. Introducer 100 also includes an inner stem distal end or terminus 110 and a hinge point 112 coupled to inner stem 108.

Introducer 100 includes a distal portion proximal region 114 that can be rotatably fixed and pivotally coupled to inner stem hinge point 112. A distal portion distal region 116 may be seen, that can be free to rotate and be rotatably coupled to distal portion proximal region 114, which is preferably not free to rotate. Lead introducer 100 also includes a distal portion distal release mechanism 117 for releasably engaging a lead head. Introducer 100 further includes an outer tube 118 that is rotatable and is coupled to a rotation coupling member, sleeve, or drive spring 120 that extends over the bendable portion 106. Rotation coupling member or drive spring 120 acts to transmit the rotation force over the bendable portion, even when the bendable portion is bent.

A pull wire, cable, or release wire 122, which can release a lead head 132 having helix electrode 134, may be seen coupled to release mechanism 117. Pull wire 122 may be controlled from proximal portion 128, which may be similar to slider 66 of FIG. 1. A push/pull rod 124, to bend portion 106, can be coupled distally to an attachment point on distal portion proximal region at 125. Push/pull rod 124 can be proximally coupled to a bending or steering proximal control element 130. Element 130 may be a rotatable knob, such as wheel 64 in FIG. 1. A rotation or torque control knob 126 can be coupled to an outer tube 118. In some embodiments, rotation or torque control knob 126 can be proximally slid to engage a pull wire coupled to transverse release member 128 by proximally translating pull wire 122. Lead head 132 may also be seen coupled to lead electrode 134 and a lead body or wire portion 136.

Figure 2B:
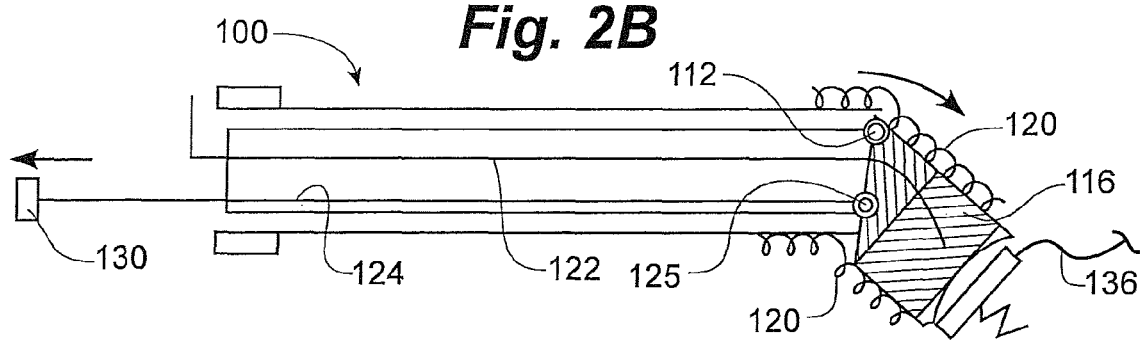
FIG. 2B is a side view of the device of FIG. 2A, having the push/pull rod proximally pulled to bend the distal bendable region.

FIG. 2B illustrates introducer 100 of FIG. 2A after steering or bending control element 130 has been proximally retracted to pull rod 124 to bend bendable steerable portion 106 to dispose distal region 116 at an angle to outer tube 118. Rotation coupling or drive spring member 120 can still transmit a rotational force over the bend, for example, for screwing a helical lead into the myocardium.

Figure 2C:
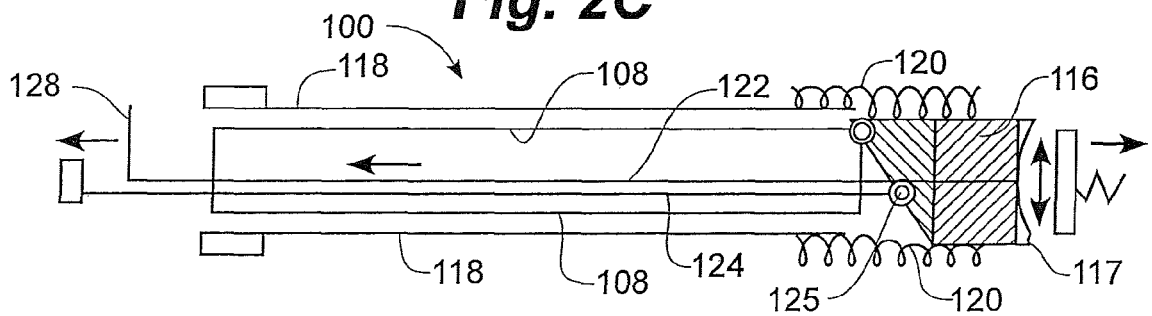
FIG. 2C is a side view of the device of FIG. 2A, having the release wire retracted to open the distal lead head engagement mechanism to release the lead head.

FIG. 2C illustrates introducer 100 of FIG. 2A after control 128 has been proximally retracted to pull on pull wire 122 to control the action of release mechanism 117. This can be done when the introducer is bent as well. As will be discussed further, release mechanism 217 can include forcing the jaws of a collet mechanism outward to release a mechanically engaged lead head. Some devices use a camming surface to open the collet jaws responsive to a pushing or pulling action on the camming surface.

Figure 2D:
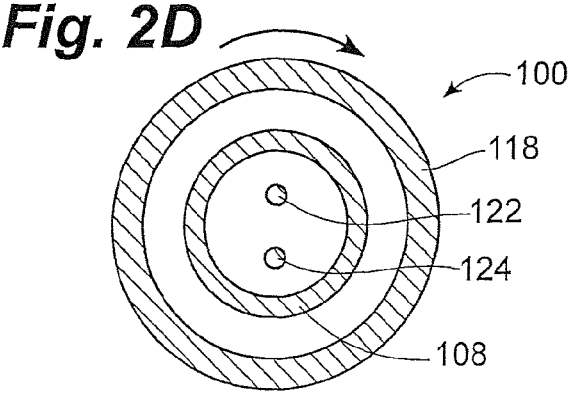
FIG. 2D is a transverse, cross-sectional view of the device of FIG. 2A, having the main outer tube rotated to rotate the drive coil over the bent distal region to rotate the distal lead engagement mechanism.

FIG. 2D illustrates outer tube 118 of FIG. 2A being rotated about inner stem 108 which in this example includes pull or release wire 122 and push/pull rod 124 slideably disposed within. Rotating outer tube 118 can cause drive spring 120 to rotate and also force distal portion distal region 116 to rotate, thereby rotating lead head 132.

The present invention can utilize many different mechanisms for achieving the different movements illustrated in FIGS. 2A-2D, and the various movements discussed elsewhere in the present application. The bending movement can be achieved using pushing, pulling, electrical, mechanical, magnetic, pneumatic, and hydraulic components. Various devices can be biased to be bent or straight, with the bias overcome with various mechanisms. Biasing can utilize any of these components as well. In one example, bellows can be used to extend over one side of the hinge and/or retract of the other side of the hinge. Electromagnetic force can be used to bend as well. Electroactive polymers can be used to achieve the bending. The rotation and release movement of the distal end can be achieved using any of the above mechanisms, forces, and components. For example suction can be used to hold the lead head and/or positive pressure used to release the lead head. The distal end lead head gripping can be biased to grip or release, depending on the embodiment.

Figure 3:
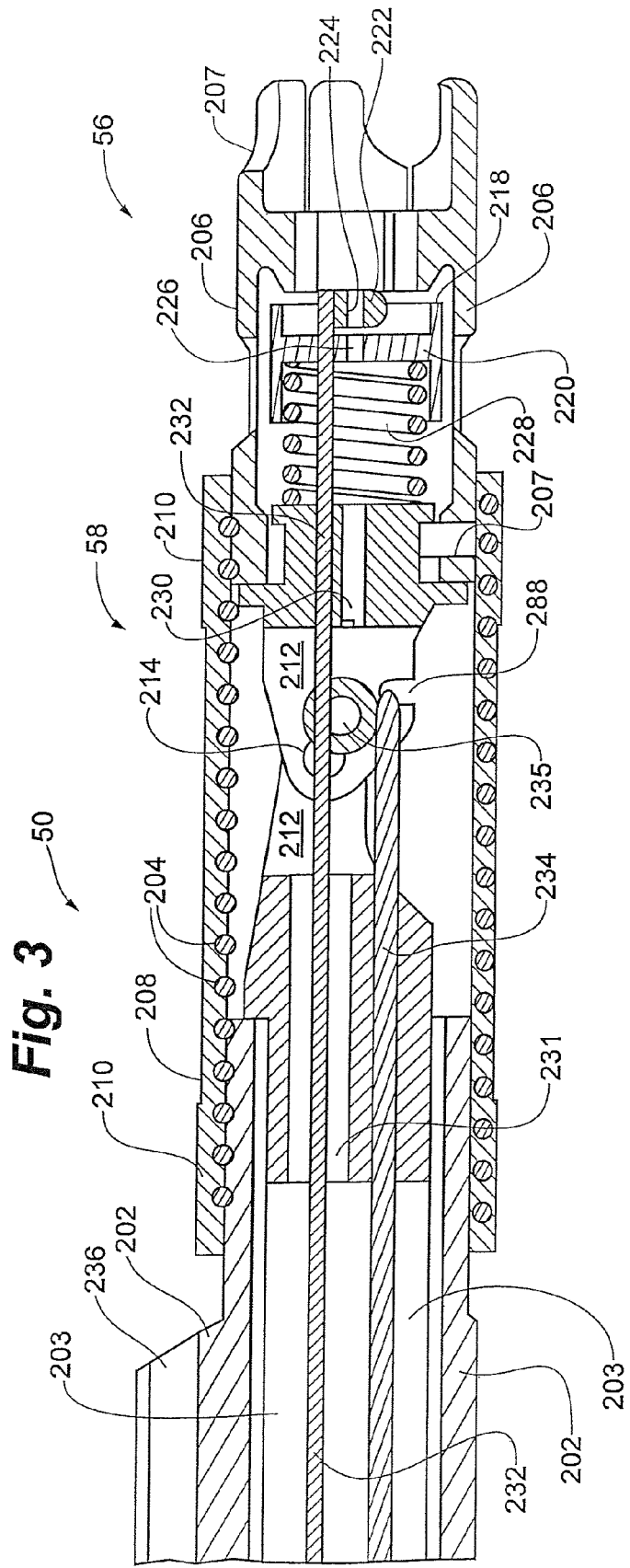
FIG. 3 is a fragmentary, side, cutaway view of the bendable distal portion of the lead introducer of FIG. 1 including a hinge, and a collet for grasping a lead head.

FIG. 3 illustrates lead introducer 50 of FIG. 1 in greater detail for bendable distal portion 58. FIG. 3 includes generally distal portion 58 and distal end 56. Some components of FIG. 3 will be described in greater detail later. Beginning with the outer regions, an outer tube 202 extends rightward and distally, having a coil spring 204 secured to outer tube 202. Spring 204 extends rightward and distally to engage the proximal portion of a collet 206. Any suitable flexible, torque transmitting coupling can be used in place of spring 204. Collet 206 includes jaws 207 for engaging a lead head. A sleeve may be seen covering coil spring 204. This sleeve, in the embodiment illustrated, includes a piece of tubing 208 bound on either end by heat shrink tubing 210. In some embodiments, tubing 208 is formed of silicone tubing. When outer tube 202 rotates, this forces coil spring 204 and collet 206 to rotate as well.

The torque flex member may be a spring. Other designs for transferring torque through an articulating joint include the use of a polymer tube, braided mesh tube made of a polymer of metal strands or the "hollow universal joint" illustrated in FIG. 15. The spring and braided tube designs can incorporate a thin highly flexible sheath that may include bellows. The sheath reduces the risk of trapping tissue in the joint during implantation. The sheath also reduces the risk that the surgical team could pinch them selves or damage their surgical glove during handling. The sheath may be made of silicone, polyurethane, latex, or other suitable biocompatible flexible polymer.

A hinge 212 is shown generally in FIG. 3, to be further discussed later. Hinge 212 is secured at the proximal end to an inner stem 203. In this example, stem 203 is a tube. In other examples, the stem is a solid shaft, having any release wires and rods extending along side. Hinge 212 pivots about a hinge pin 214. This pivoting can be caused by a push/pull rod 234, which in this embodiment has a distal protrusion for engaging part of the hinge at 280. Thus, pulling on push/pull rod 234 causes collet 206 to bend downward, while pushing on push/pull rod 234 causes collet 206 to again become more axially aligned with stem 203 and outer tube 202.

Collet 206 includes inner wedges 216. Wedges 216 can be engaged by a wedge ring 220 having a wedge ring leading edge 218. A spring 228 may bear against wedge ring 220, urging leading edge 218 against the inside of wedges 216, thereby urging collet jaws 207 to close about a lead head. Hinge 212 may be seen to have a proximal channel 231 and a distal channel 230 for accepting a pull wire 232, shown above channels 230 and 231 in order to make the channels visible. Pull wire 232 can ride over a cylinder rotating about a pin 235, to aid in releasing the lead head when the hinge is bent. Pull wire 232 extends further distally through compression spring 228, through a wedge ring channel 226, and further through a crimp slug channel 224 formed in a crimp slug 222.

Thus, when no tension is being applied to pull wire 232, compression spring 228 forces wedge ring against wedges 216 to urge jaws 207 to a closed position. When tension is applied to pull wire 232, the force of compression spring 228 is relieved and wedge ring 220 travels proximally, away from wedges 216 to allow collet jaws 207 to open and release the engaged lead head. Hinge 212 may be seen to have a distal portion distal of hinge pin 214 that pivots but does not rotate relative to inner stem 203. Collet 206 does rotate relative to inner stem 203. Collet 206 is allowed to rotate, in some embodiments, through the use of a collet clip ring 207 which allows rotational movement of collet 206 about hinge 212, but prevents axial movement of collet 206 with respect to hinge 212.

Figure 4:
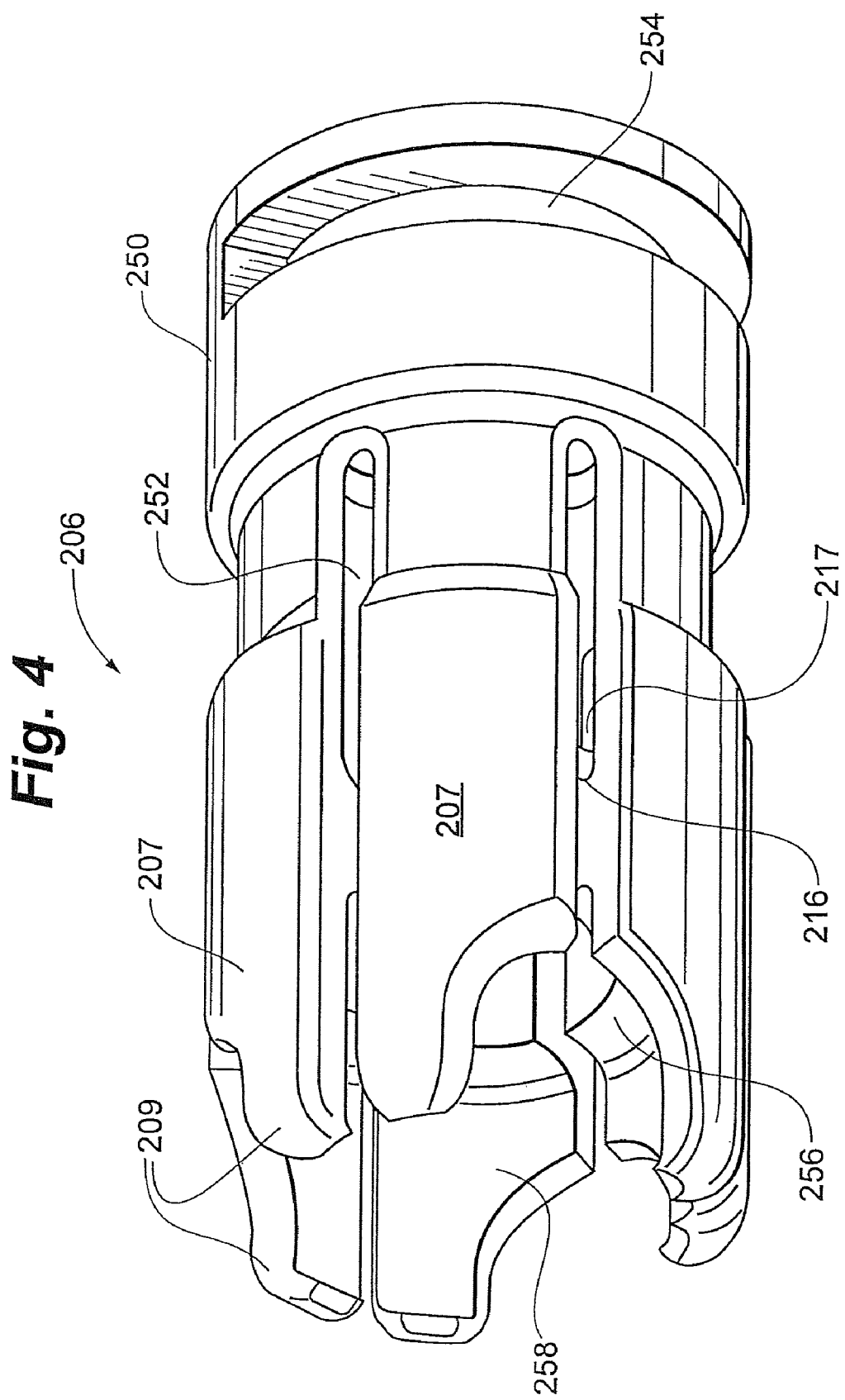
FIG. 4 is a perspective view of the collet of FIG. 3.

FIG. 4 shows collet 206 in greater detail. Collet 206 includes jaws 207, having slots or cutouts 252 there between and a generally open distal area 258 for receiving a lead head. Teeth 209 may be seen protruding radially inward and forming an inside diameter or profile less than the outside diameter of the lead head to be grasped. In some devices, the jaws and collet are dimensioned to compress the lead head with the teeth. A distal lip or ledge 256 may be seen for abutting the lead head. One inner wedge 216 may be seen, having a proximal cavity 217 for receiving the wedge ring. Collet 206 also includes a proximal region 250 including a slot 254 for receiving the collet clip ring. Collet 206 can thus receive the wedge ring within for bearing against wedges 216 and also receive spring 228 (not shown in this figure) for urging the wedge ring against the wedges.

Figure 5:
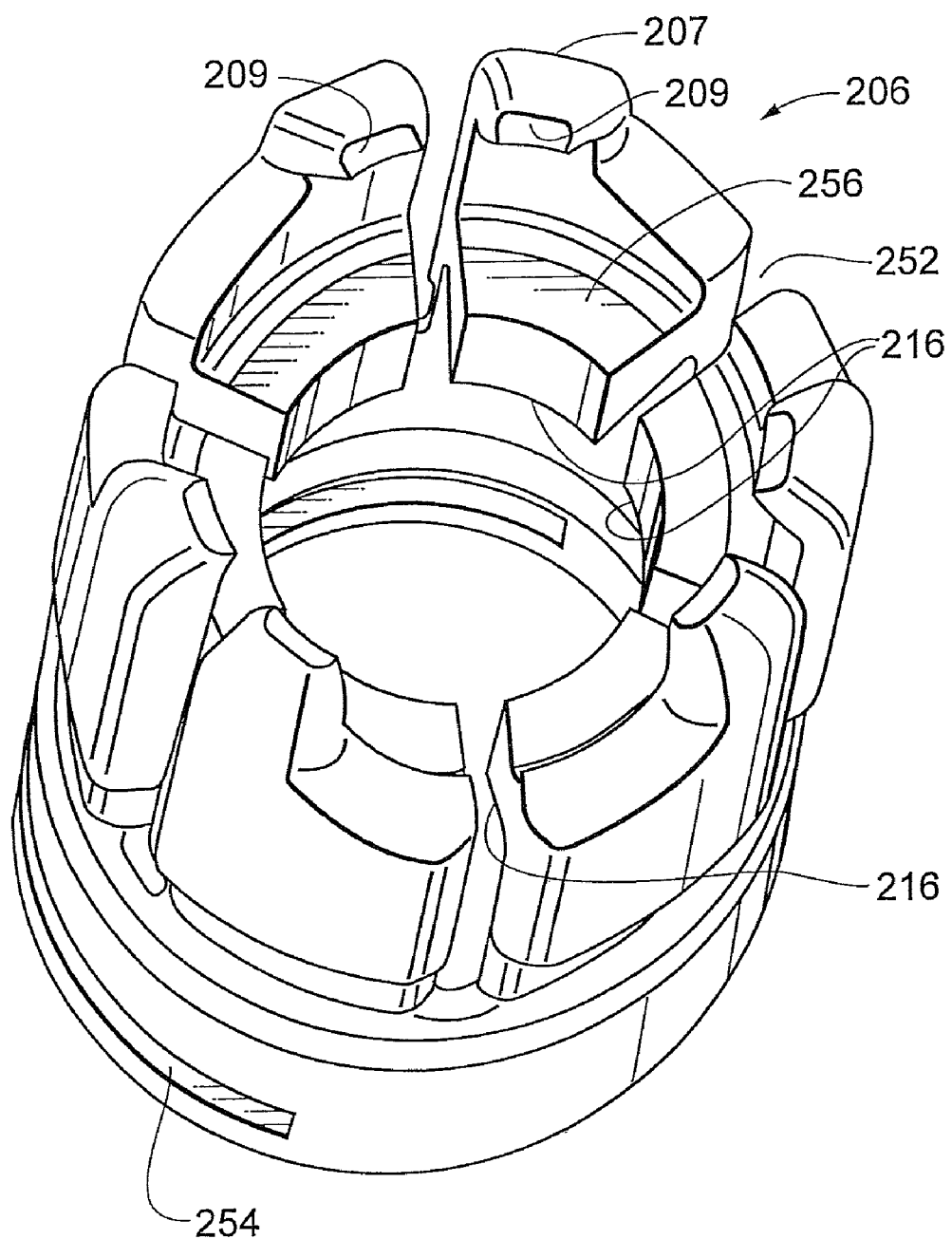
FIG. 5 is another perspective view of the collet of FIG. 3.

FIG. 5 also shows collet 206, again having jaws 207, teeth 209, slots 252, lip 256, clip ring receptacle 254, and wedge 216. In various embodiments of the invention, the number of teeth are configured so that the lead head is surrounded, having an angle no greater than about 120, 100, 90, or 80 degrees, depending on the embodiment, between the edges of adjacent teeth. The collet illustrated has an angle of less than about 80 degrees between adjacent teeth sides. The collet incorporates engagement features that provide for mechanical engagement with the outside perimeter of the pacing lead head. The collet can encompass 360° of the pacing lead head with multiple cut outs that provide for routing of the lead body and release motion. The mechanical engagement features of the collet may interlock with design features in the head. A pulling, tension force can be applied to the lead head when it is loaded in the lead engagement mechanism, and the force can put the engagement features in shear. Engagement of the lead head may also be accomplished by providing sufficient force to the collet engagement features so that they deform the material (e.g. low durometer silicone) of the lead head around the collet features. The deformed material would oppose a tension force applied to the lead head through material shear. The collet can be retained on the forward hinge portion by a snap ring/retainer that bears against the set of the smallest distal ID of the forward hinge portion.

Figure 6A:
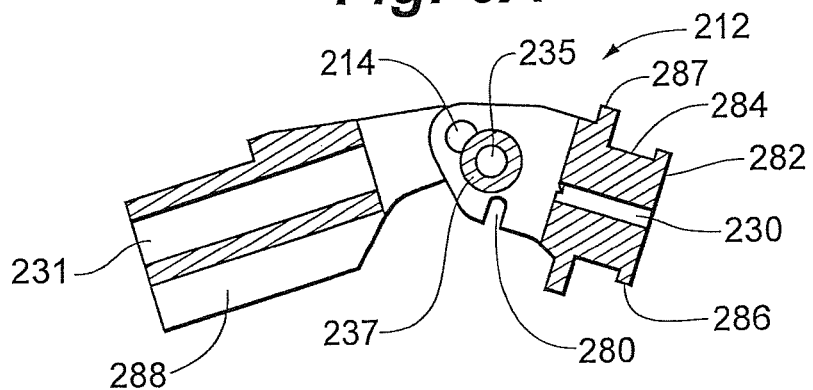
FIG. 6A is a side, cross-sectional view of the hinge member of FIG. 3.

FIG. 6A illustrates hinge 212 in greater detail. Hinge 212 includes forward central channel 230 and rear central channel 231, as previously described, for receiving the pull wire to release the collet engagement mechanism. Hinge 212 also includes hinge pin 214 and a second rear channel or slot 288 for receiving the push-pull wire to bend hinge 212. The push-pull wire can be accessed from within slot or recess 280, and may also have the end of the push-pull wire received within an orifice in the opposing side of the hinge. Pin 235 and cylinder 237 are shown. Hinge 212, in the embodiment illustrated, also includes a distal face 282 which can be used to urge the compression spring against the collet mechanism. Hinge 212 can also include a distal lip 286 bounding an annular channel or recess 284 followed proximally by a more proximal lip 287. Annular channel 284 can be used to secure the collet to hinge 212 through use of the collet clip ring, previously described. The collet can thus rotate about annular recess 284, with travel in the axial direction limited by lips 282 and 287.

Figure 6B:
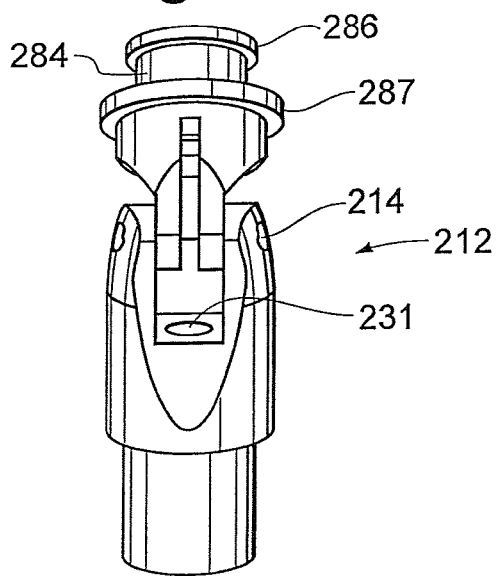
FIG. 6B is a top, perspective view of the hinge member of FIG. 6A.
Figure 6C:
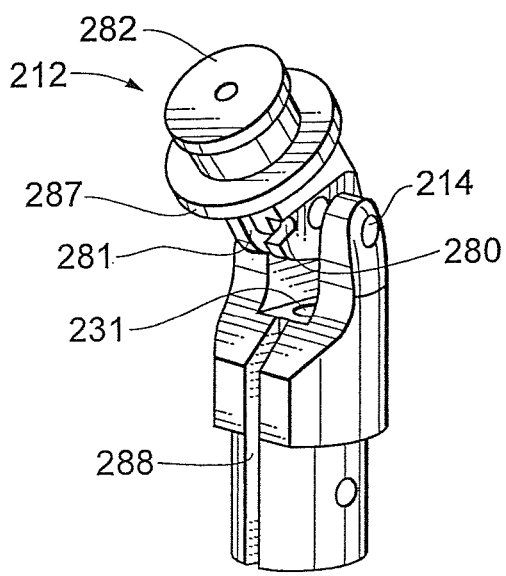
FIG. 6C is a bottom-side, perspective view of the hinge member of FIGS. 6A and 6B.

FIG. 6B illustrates hinge 212 in a top, perspective view. Annular recess 284 is further illustrated, as is the proximal extent of rear channel 231 for receiving the pull wire. FIG. 6C illustrates hinge 212 from the side and bottom, better illustrating slot or channel 288 for the push-pull rod. Channel 288 can guide the push-pull rod, and may have a hole 281 for receiving the bent end of the push-pull rod.

An alternative articulating joint design utilizes a "living hinge" configuration. A living hinge relies on the plastic properties of a material for the movement in the joint. Living hinges are commonly made in plastic products for attaching a cover to a housing. Polypropylene and polyethylene are common materials used for plastic living hinges. A thin metal strap could also be utilized to join the distal and proximal components of the joint. The use of a metal strap would require design modifications to the rear hinge and the forward hinge. If utilizing a plastic living hinge it may be possible to incorporate the rear hinge, forward hinge, and hinge itself into one molded component. The use of a living hinge may allow the diameter of the hinge to be decreased; this would allow the overall diameter of the shaft of the device to decrease.

Figure 7A:
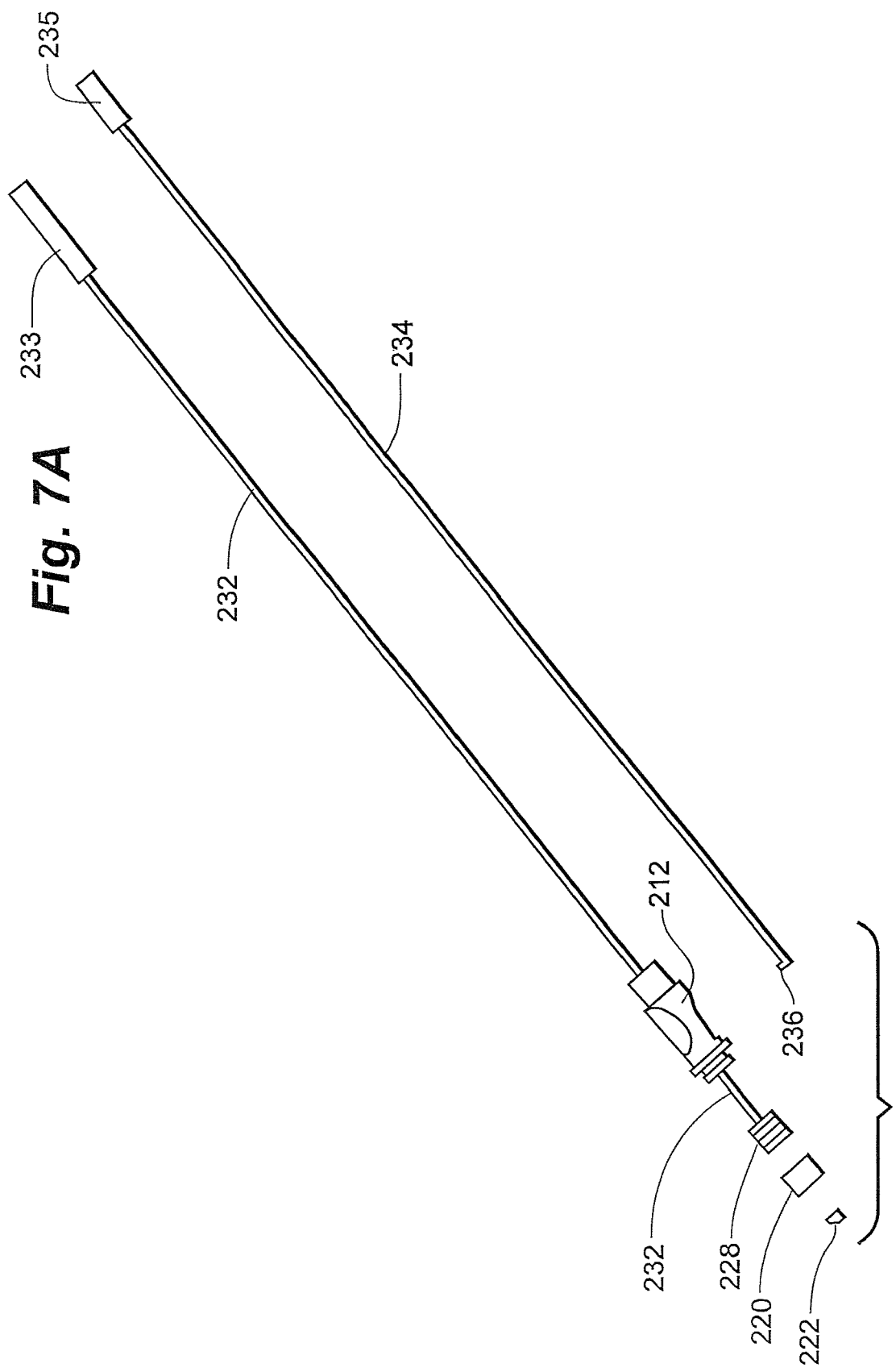
FIG. 7A is an exploded view of a distal portion of the lead introducer of FIG. 1 including the hinge of FIG. 6A, having a collet release wire extending therethrough and a push-pull rod to bend the hinge disposed alongside.

FIG. 7A illustrates hinge 212 in conjunction with other components, in an exploded view of introducer 50. Pull wire 232 may be seen extending through hinge 212, having wire proximal portion 233 that is wider than the more distal regions in some embodiments. Pull wire 232 may be seen extending through compression spring 228 that has wedge ring 220 in front of the compression spring, followed by crimp slug 222 for binding the wire. The assembling of these components may be visualized with respect to this figure by distally advancing pull wire 232 through spring 228 and further through wedge ring 220. Crimp slug 222 can then be disposed about pull wire 232 and crimped. Pull wire 232 can then be proximately retracted, thereby urging wedge ring 220 against compression spring 228, which in turn is urged against hinge 212. Push-pull wire 234 may also be seen, having both a distal hook or protrusion 236 and a more proximal, wider portion 235. The assembling of push-pull wire or rod 234 may be visualized by moving push pull rod 234 toward hinge 212 until distal hook 236 engages hinge aperture 281 (illustrated in FIG. 6A).

Figure 7B:
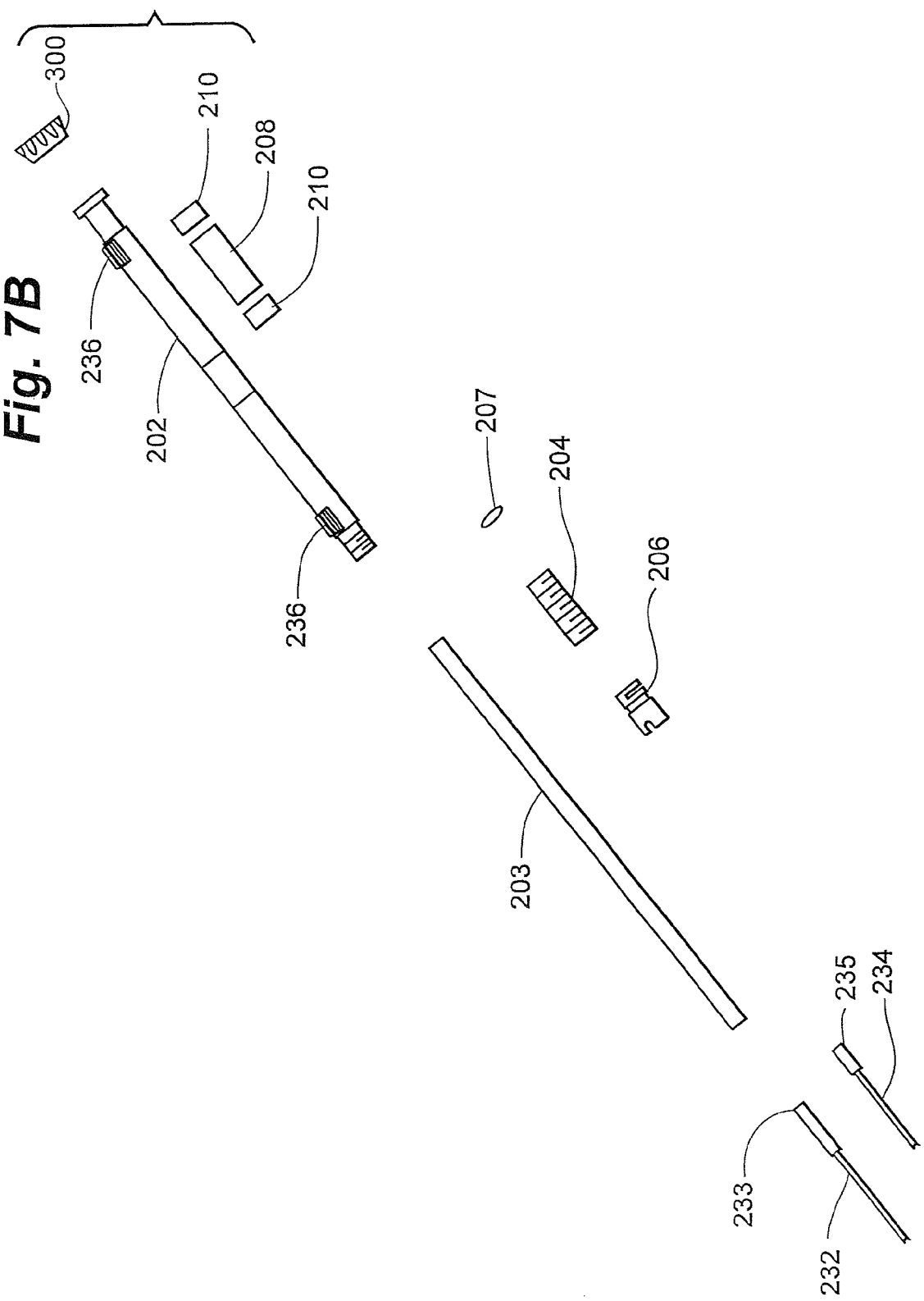
FIG. 7B is an exploded view of the midsection of the lead introducer of FIG. 1 including the inner stem, the outer rotatable tube, the collet, and the drive spring for disposing over the hinge of FIG. 6A.

FIG. 7B illustrates the mid-region of lead introducer 50 in greater detail. Inner stem or tube 203 is illustrated, as is collet 206 and outer coil spring 204 which can be eventually disposed over the hinge. Collet clip ring 207 is shown for securing collet 206 to hinge 212. The outer sleeve or tubing 208 is illustrated; together with the proximal and distal heat shrink sections 210 which can be used to fix the flexible sleeve over coil spring 204 and bendable hinge 212.

The introducer stem 203 can be the "back bone" of the "stationary skeleton" in some devices and can provide sufficient rigidity to support the distal lead engagement mechanism and the related forces during manipulation of the device. Typically the stem will be constructed out of a medical grade stainless steel; reinforced polymers or other metals may be used. When the stem or shaft is tubular, the lumen of the tube provides passage for the push/pull rod and the pull cable. The proximal end of the introducer stem can be inserted into the handle.

Outer tube 202 is illustrated, having lead management devices in lead retainers or guides 236. Lead retainers 236 can allow the lead to be carried about the rotating outer tube 202 while yet allowing for the carried lead to be slid axially, caused by the bending movement of the hinge and the lead head carried at the distal end of the hinge.

The assembling of the mid-region may be visualized with respect to FIG. 73, together with the end result of the previous assembly previously described with respect to FIG. 7A. Pull wire 232 having proximal region 233, and push pull rod 234 having proximal region 235, may be inserted through tube 203. As previously discussed, pull wire 232 may have been secured through hinge 212, and push pull rod 234 secured to hinge 212. This assembly method, and other assembly methods described herein may be varied of course depending on the embodiments and methods used. Collet 206 may be abutted to wedge ring 220 and secured to hinge 212 using wedge ring retainer clip 207 (illustrated in FIG. 7A). Inner tube 203 may be inserted into outer rotatable tube 202. Coil 204, then sleeve 208 and heat shrink portions 210 may be slid over stem 203 to cover hinge 212 and heat shrunk into place.

FIG. 7C illustrates the handle portion of introducer 50, including a knob ring 302 for being disposed over outer tube 202 and a release lever 304 which will ultimately be secured to the pull wire. Release lever 304 includes the release or gripping head 66, as previously illustrated.

Pull wire 232 proximal region 233 can be entirely slid through outer tube 202 as can pull wire 234 proximal region 235. With knob ring 302 slid over the proximal end of outer tube 202, release lever 304 can be moved to receive proximal region 233 within the lower portion of the release lever. Nut 306 can then be threadably secured over proximal region 233, securing pull wire 232 to lever 304. Another nut can be slid within rod linkage 308, the rod linkage advanced, and push-pull rod proximal region 235 threadably secured to the nut within rod linkage 308. Rod linkage 308 can ultimately have proximal region 309 controlled by the deflection wheel 64, illustrated in FIG. 1.

The deflection wheel 64 includes a left half 318 and a right half 320. Similarly, handle 52 includes a left half 314 and a right half 316. Left wheel half 318 can be disposed about an axial nub within handle left half 314. Rod linkage proximal region 309 can then be secured to wheel left half 318. A protrusion on the rod linkage can be received within a slot in wheel 64 in some devices. This can bring release lever 304 release head 66 within a handle aperture 315. Rotation knob 62, illustrated in FIG. 1, can be formed by bringing together knob top half 310 and knob bottom half 312. Wheel right half 320 can be secured to wheel left half 318 and handle right half 316 secured to the wheel and handle left hand side 314. The knob top half and bottom half can be secured together and knob ring 306 moved proximally over the now complete rotation knob 62. Release handle 66 thus can be used to move the pull wire, wheel 64 can be used to move the push pull rod through rod linkage 308, and knob 62 can be used to rotate outer tube 202.

FIG. 8 further illustrates the handle portion, having elements as previously numbered and described. A protrusion 237 on rod linkage proximal region 309 can be received within an arcuate slot 236 in wheel 64 for transforming a wheel rotation into a linear actuating motion for the push-pull rod to effect bending.

Figure 9:
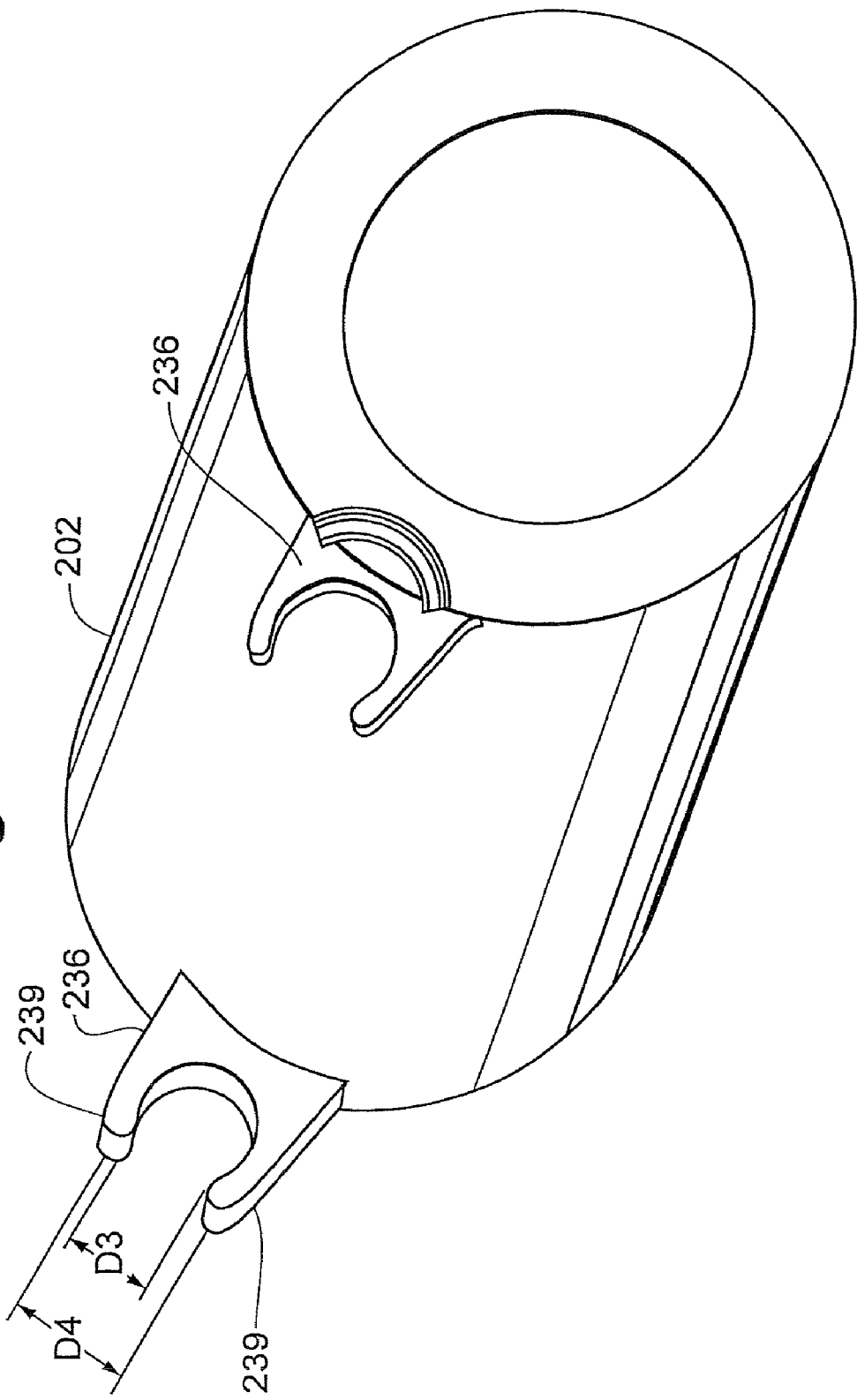
FIG. 9 is a perspective view of the rotatable outer tube of FIG. 1, having undercut lead management guides thereon.

FIG. 9 illustrates lead guides 236 on outer tube 202. In the example illustrated, lead guides 236 are undercut, having a narrower top opening and a wider opening away from the top. The lead guides in some embodiments act as elastic jaws, being elastically displaceable to allow a lead body to be formed into the guide, with the jaw then closing to inhibit radial movement of the lead out of the guide. In other embodiments, the lead guides are not very elastic, but the lead body deforms elastically when passed through the narrow jaws. In one example, the lead body is formed of silicone or polyurethane, and the jaws are formed of Lexan® polycarbonate. Axial movement of the lead is still allowed, due to the lead guide opening being larger than the lead outer diameter in the guide center but not further away from the tube. In the example, illustrated, the guide jaws are a distance "D3" apart, while the main portion of the guide has a larger inside diameter, indicated at "D4."

FIG. 10 illustrates a collet 450 coupled to a pull wire or cable 452. A collet wall 454 may be seen including a collet undercut region 462. A Bellville washer 456 may be seen coupled to pull wire or cable 452. A lead head 458 may be seen having a tapered sidewall 460. In some embodiments, lead head 458 has straight sidewalls, formed of a polymeric material, that are engaged by collet undercut region 454. A lead electrode, a helical electrode 464 may be seen.

FIGS. 11A and 11B illustrate a collet release mechanism 700 including collet jaws 702 having an annular grove 703 in the sidewalls. A release cable or wire 704 is seen coupled to a Bellville washer 706. Washer 706 may be seen in a first, closed position 708 and a second, radially expanded position 709 for forcing apart collet jaws 702.

FIGS. 11A and 11B illustrate an alternative design that utilizes a clover spring or Bellville washer that is positioned with the concave side facing away from the distal tip. When the pull cable is placed in tension the spring/washer is flattened leading to an increase in effective diameter of the spring/washer that opens the "collet". FIG. 11A illustrates the closed or lead engaged position while FIG. 11B shows the open or lead released position. In FIG. 11A the diameter (D1) is less than the diameter in 11 B (D2). The normal position for this design is closed. The force to "close" the collet comes from the plastic properties of the washer material. A wide range of polymers may be utilized in addition to appropriate metal alloys.

Figure 12A:
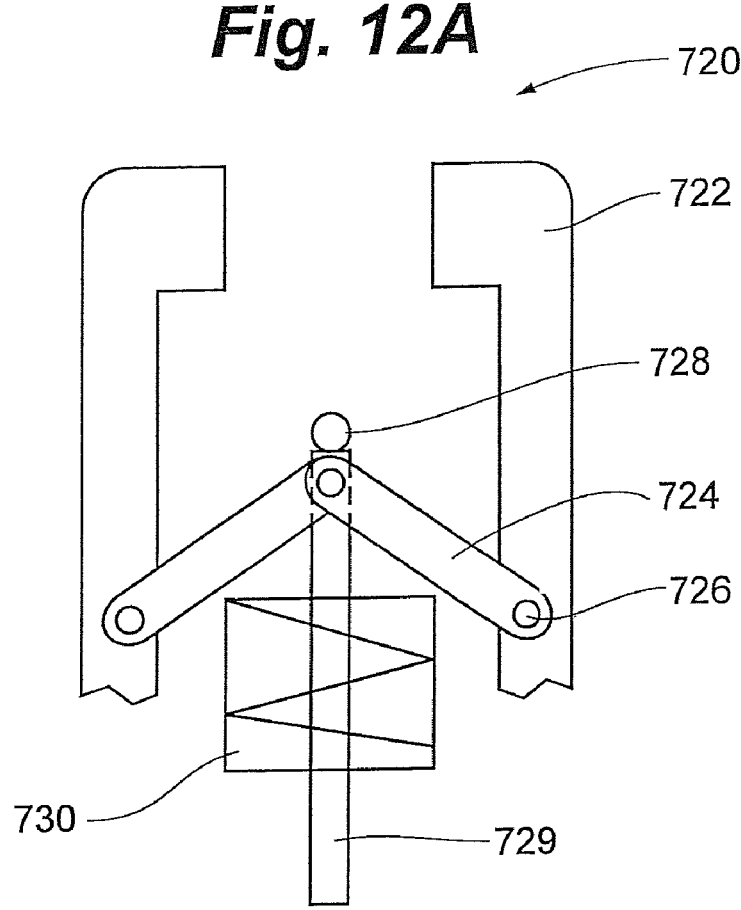
FIGS. 12A and 12B are fragmentary, side views of a four-link mechanism for expanding the jaws of a collet outward to release an engaged lead head.
Figure 12B:
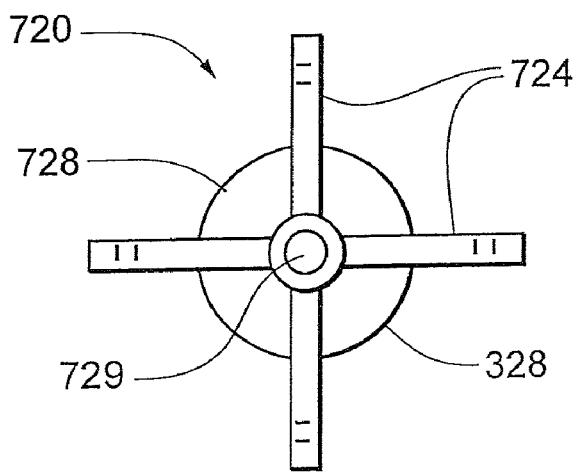

FIGS. 12A and 12B illustrate a collet release mechanism 720 including collet jaws 722. Four linkages 724 may be seen coupled to collet jaws 722 through pins 726. A link header 728 may be seen joining the four links. A spring 730 may be seen for distally biasing links 724 to bias collet jaws 722 closed. A pull cable 729 may be seen coupled to link header 728 for proximally retracting header 728 to force links 724 against jaws 722 to open the collet mechanism and release the electrode head.

Figure 13:
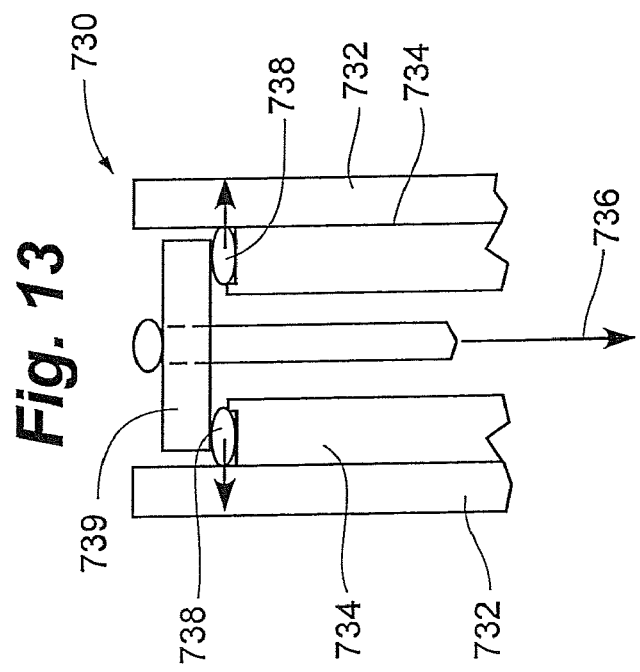
FIG. 13 is a fragmentary, side view of a mechanism for expanding apart the jaws of a collet by forcing a squashable polymer outward to force the jaws outward when the pull cable is retracted to foreshorten the polymer O-ring.

FIG. 13 illustrates yet another collet release mechanism 730 including collet jaws 732 forming a radially free wall portion 732. Rigid walls 734, not being freed to radially expand outward, may also be seen. A pull wire 736 is slideably received within rigid walls or tube 734 and is coupled to a washer 739. An O-ring 738 may be seen disposed between washer 739 and the distal end of rigid walls 734. When pull wire 736 is proximally retracted, O-ring 738 expands regularly outward, to force the collet jaws or free walls 732 outward which can act to release a retained lead head. FIG. 13 thus illustrates an alternative mechanism that utilizes the polymer's Poisson's ratio. When tension is placed on the cable/rod the washer compresses the toroidally configured polymer part, which is captured by rigid members on two sides. The outside or free wall of the collet is pushed outward by the "hydraulic" like action of the compressed polymer.

Figure 14:
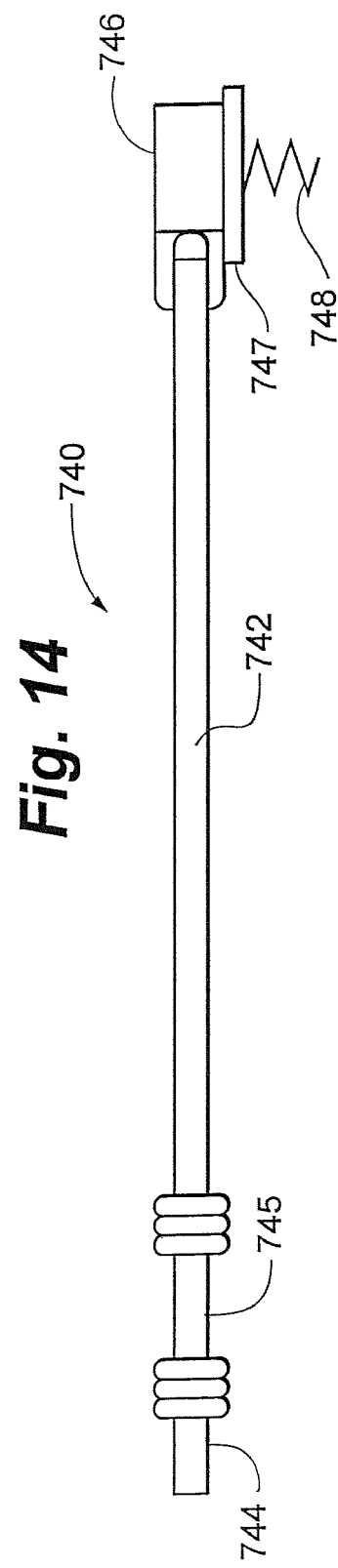
FIG. 14 is a side view of a myocardial bipolar pacing lead.

FIG. 14 illustrates a bipolar pacing lead 740 comprised of three main portions: a distal electrode end 747, a midsection or lead body 742, and two proximal connectors 744 and 745. It is common for the lead body of myocardial/epicardial electrodes to enter a distal head 746 perpendicular to the axis of helical electrode 748. During implantation it is not normally desirable to maintain the lead in the perpendicular orientation because it would require substantial room during rotation. With commercially available rigid lead implant tools (BIOMEC 100449001 and Medtronic 10626) the lead is gently bent proximally from the head allowing the lead body to be positioned parallel with the center axis of the helix. In this arrangement the entire implant tool is rotated and the orientation of the lead body to the head is maintained.

The perpendicular orientation of the body to the head becomes a challenge when an articulated joint is used in the design of the implant tool. When an angle of articulation is instituted during the implant procedure rotation of the entire implant tool would require swinging a substantial radial path with the proximal end of the tool. This is often not feasible because of the limited space in the thoracic cavity, through a port, or through an intercostals or subxiphiod incision.

Figure 15:
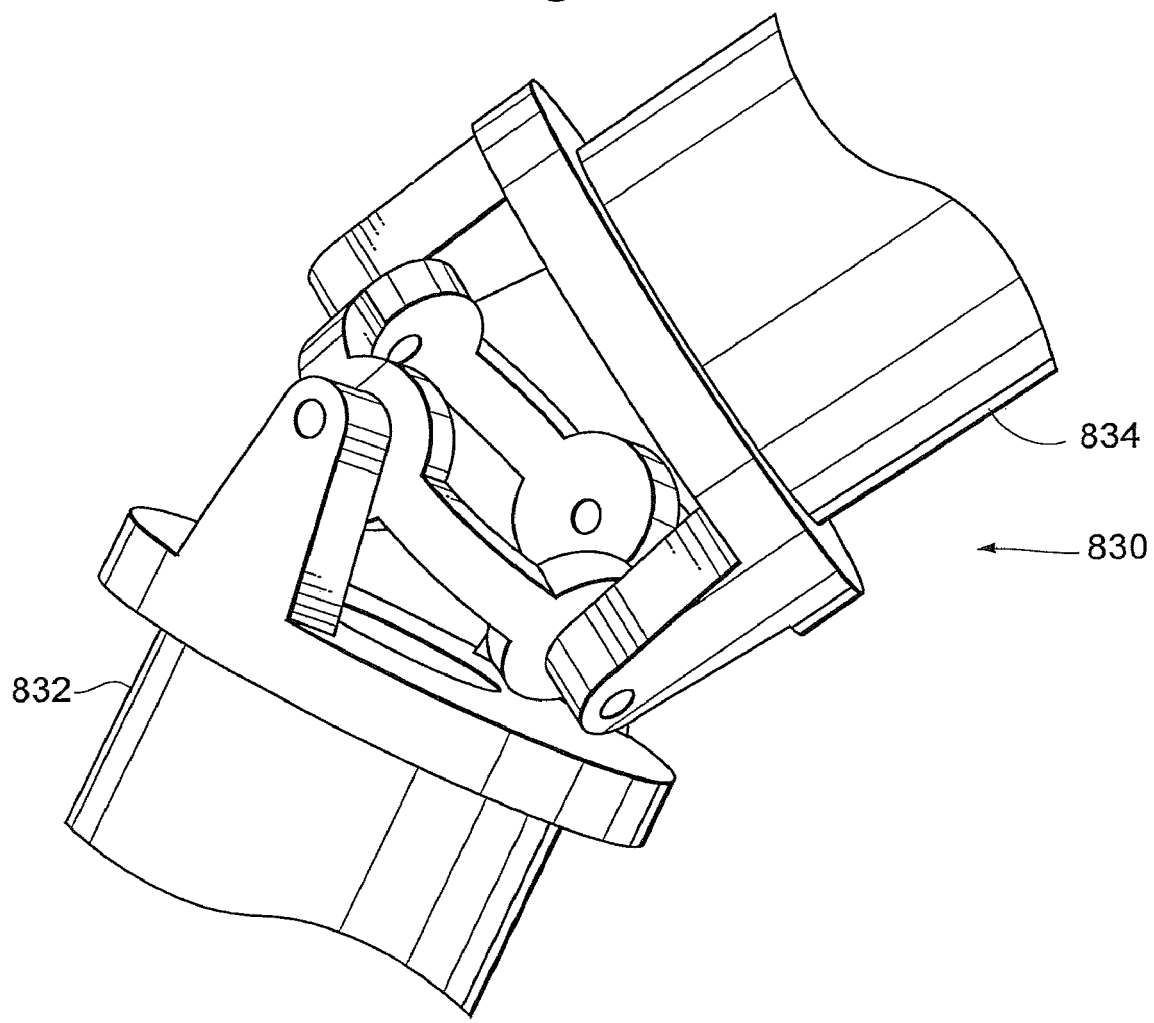
FIG. 15 is a fragmentary, perspective view of a hollow universal joint for forming the rotatable and bendable distal portion of a lead introducer.

FIG. 15 illustrates a hollow universal joint mechanism 830 including a distal hinge portion 832 and a proximal hinge portion 834. A pull wire may be received through the U-joint and may ride over pulleys. Pins, or other guides within the joint. Hollow universal joint mechanism 830 can be used to implement the distal, bendable region of the lead introducer in some embodiments.

Figure 16:
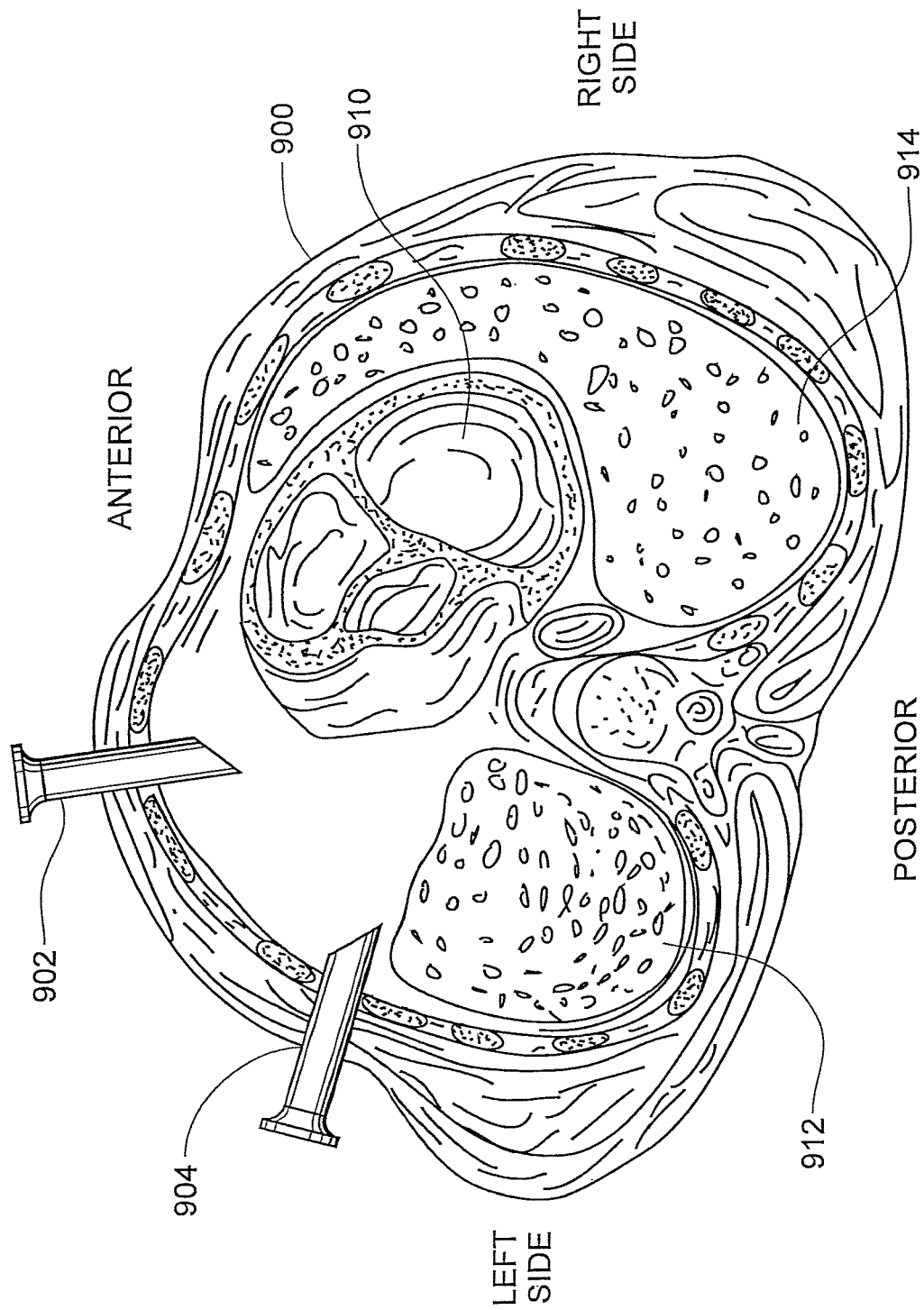
FIG. 16 is a superior to inferior view through a patient having the left lung deflated and a tool and a scope inserted into the chest.

FIG. 16 is a superior to inferior view of a person 900 having a left lung 912 that has been deflated and a right lung 914. Heart 910 may be seen as well. A port 902 for admitting a scope may be seen, as may a second port 904 for admitting tools. The lead introducer according to the present invention can be admitted through port 904, which may have a 15 mm ID.

Figure 17:
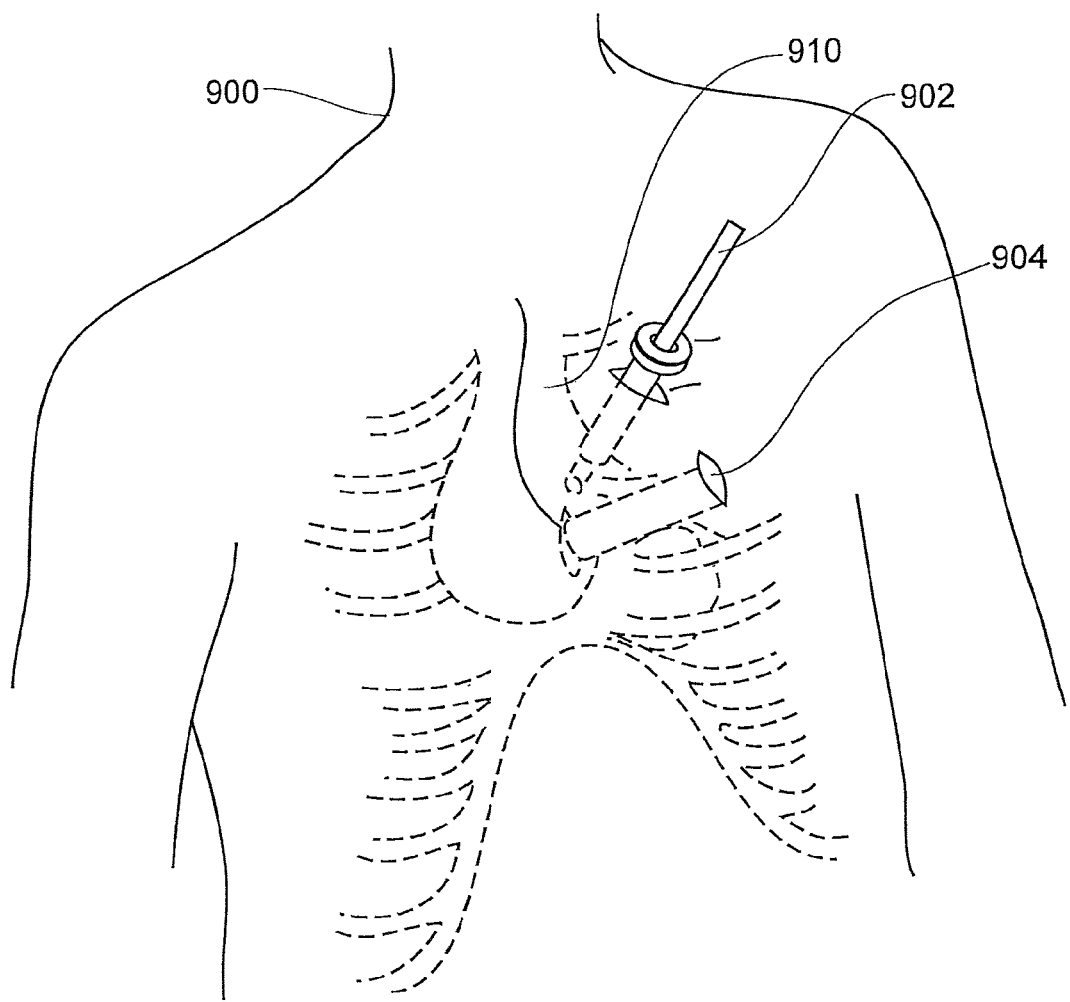
FIG. 17 is a highly diagrammatic front view of a patient having a tool and scope inserted to access the heart.

FIG. 17 further illustrates ports 902 and 904 of the present invention. As may be seen from inspection of FIG. 17, the lead introducer may be admitted through port 904 in a straight approach, followed by bending the distal bendable portion to present the lead helical electrode directly toward or normal to the epicardial surface. Even a relatively long, straight portion of the port presents no problem for admitting the straight, lead introducer that can be bent or curved after passage into the body.

Figure 18:
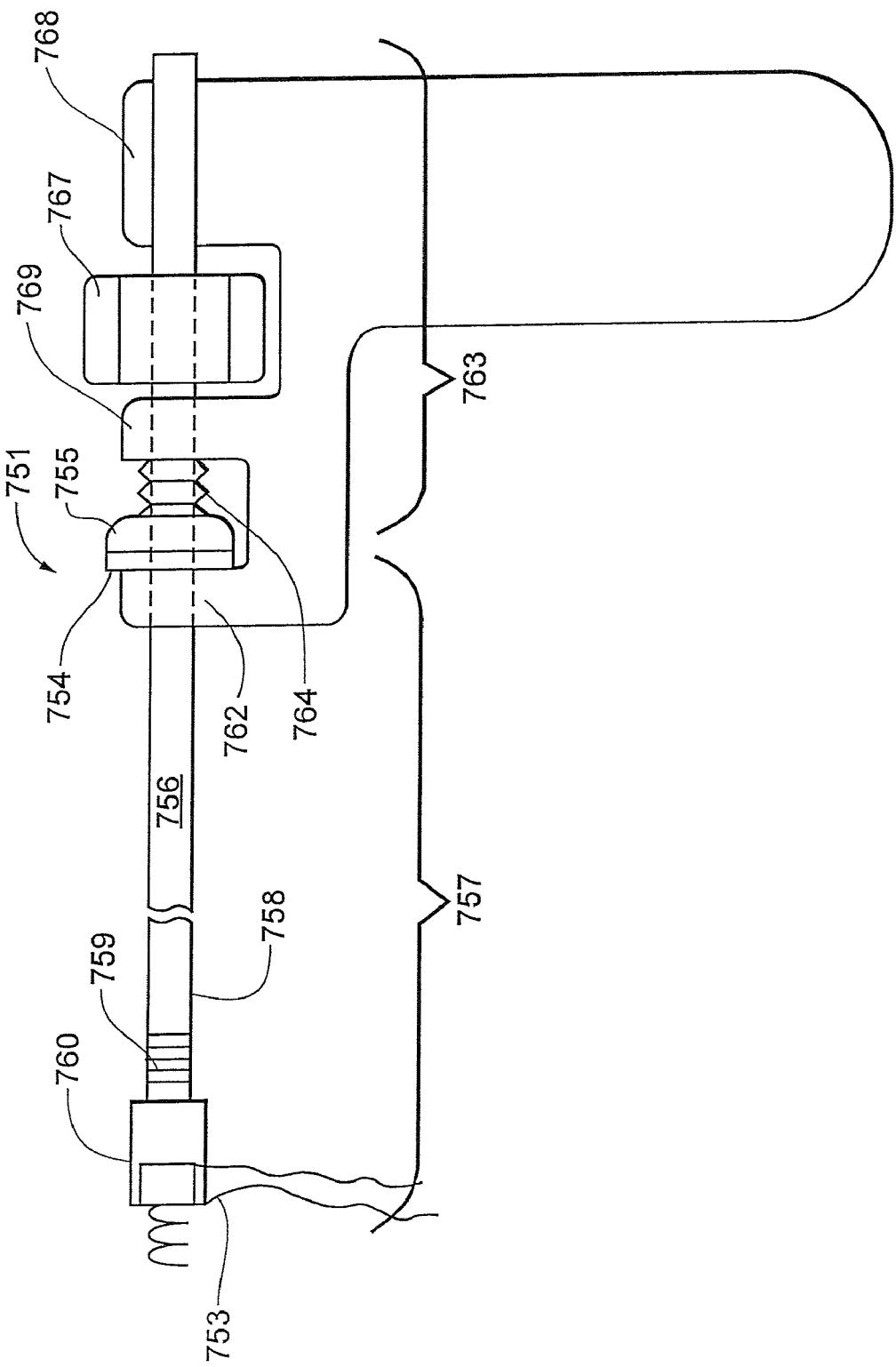
FIG. 18 is a highly diagrammatic side view of an alternative lead introducer having a friction safety clutch.

FIG. 18 illustrates a lead introducer 750 having a friction safety clutch 751. During the implantation of a screw-in epicardial/myocardial pacing lead 753 the implanter prevents over turning the lead by counting the number of turns. During a minimally invasive procedure the implanter may not be able to tell when the helical electrode engages the cardiac tissues, so it is, difficult to know what the correct number of turns is. If the helix is turned too many times, this could possibly lead to poor lead fixation and higher impedance or poor pacing parameters.

The integration of the "torque limiter" into the drive shaft of the implant tool would limit the amount of torque applied to the screw-in pacing lead. The implanter would not have to rely on counting the number of turns to know when he has fully seated the lead. The implanter would continue to rotate the torque knob until a friction plate 754 slips with respect to a friction plate 755. A visual indicator or marking could be incorporated into the two plates to make the "slippage" obvious to the implanter.

The implant tool with integrated "torque limiter" could be used for implant of other screw in stimulation leads such as in gastric stimulation, neuro stimulation, etc. The concept could also be applied to other surgical implants that require screwing in fixation devices; this could include bone anchors, hernia repair patch anchors, etc.

FIG. 18 illustrates an introducer stem or drive shaft 756 split into two portions with a distal portion 757 encompassing friction plate 754, a length of the introducer stem/drive shaft 758, components of an articulation joint 759, and the lead engagement mechanism 760. The distal portion of the drive shaft passes through and is supported by the distal handle journal 762. The proximal portion 763 of the drive shaft encompasses friction plate 755, pressure spring 764, and torque knob 767. The proximal portion passes through and is supported by a mid-handle journal 769 and may also make use of a proximal handle journal 768.

The screw in style myocardial pacing lead is held by the lead engagement mechanism at the distal end of the implant tool. The user rotating the torque knob located in upper portion of the handle rotates the screw electrode/lead. The rotation of the torque knob 767 is transmitted by the proximal portion of the introducer stem to friction plate 755. The spring applies a force to the back of friction plate 755 to cause sufficient friction between friction plate 755 and friction plate 754. The torque transfers from friction plate 754 through the distal portion of the drive shaft through any articulation joint that is used to the lead engagement mechanism. The lead engagement mechanism thereby rotates the helical screw electrode into the tissue.

Figure 19:
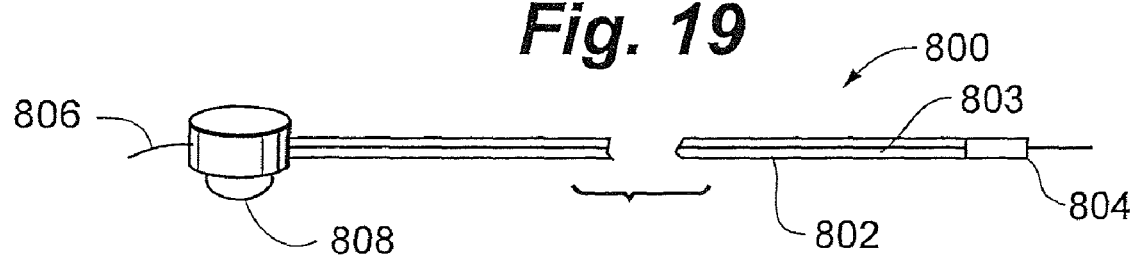
FIG. 19 is a side view of a mapping lead having a button electrode.
Figure 19A:
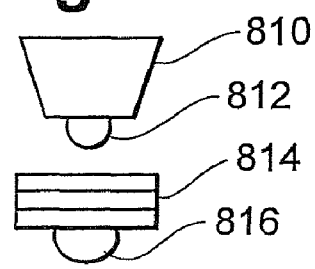
Figure 20:
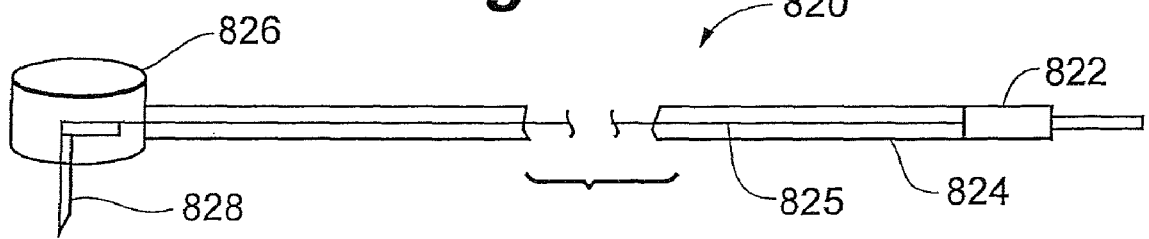
FIG. 20 is a side view of a mapping lead having a needle electrode.

FIGS. 19 and 20 illustrate mapping leads 800 and 820 that can be used with lead introducers. The use of a permanent pacing lead such as the BIOMEC 511210 requires screwing the helical electrode into the myocardium. If the selected implant site does not produce the target pacing performance may require removal of the lead. Removal of the lead may lead to some bleeding or undesirable tissue trauma. To avoid implantation of a screw in epicardial/myocardial and the potential that it may need to be removed, the implanter may at times wish to test the pacing characteristics of a implant site prior to implanting a permanent pacing lead.

The two designs (button electrode lead 800 in FIG. 19 and needle electrode lead 820 in FIG. 20) are designed to map the EP parameters of the heart with less trauma to the heart than a screw in pacing lead. The button electrode can be used on areas of the heart where there isn't fat. The needle electrode may be used in areas where fat exists because it will penetrate through the fat.

The mapping electrode and implant tool could be used for mapping and or temporary stimulation studies prior to implantation of other screw in stimulation leads such as in gastric stimulation, neuro stimulation, etc.

Referring again to FIGS. 19 and 20, two temporary mapping and stimulation electrodes for use with a remotely steerable lead introducer are illustrated. The distal portion of the temporary lead is comprised of the heads 806 and 826 and electrodes 808 and 828. Load 800 includes a lead body 802, connector pin 804, conductor 803, lead head 806, and button electrode 808. Alternate lead head profiles are indicated at 810, having an undercut profile and button electrode 812, and at 814, having a grooved profile and button electrode 816. Lead 820 has a lead body 824, a conductor 825, a lead head 826, and a needle electrode 828. The head can have a similar diameter and geometric configuration to the BIOMEC 511210 with a general diameter of 0.280-0.300". The head can be made from any number of biocompatible polymers that are acceptable for short-term blood and tissue contact; examples include silicone, polyurethanes, polysulphones, etc. The head can serve three functions in some embodiments: (1) provide a means for mechanical engagement with the implant tool; (2) mechanically hold and maintain the orientation of the electrode in relation to the lead body and implant tool; and (3) act as a stop to prevent the electrode from penetrating the tissue too deeply.

The design intent for the electrode is to effectively, with little or no tissue damage, transmit electrical signals form the heart to a pacing system analyzer and or send stimulation signals from a pulse generator or system analyzer to the tissue. The best performing electrodes are made from platinum/iridium, titanium, etc. with any number of coatings including porous platinum, titanium nitride, etc. Electrode surface areas, along with surface finish, also have an impact on the performance parameters of the electrode.

The long flexible mid-section is called the lead body and can range from 20-55 cm long. The lead comprises a conductor that is surrounded by an insulator. Since this application is short term, a savings can be realized by the use of inexpensive conductor materials and shapes. A single strand of annealed copper may perform satisfactorily in this application. The lead outer body can be made from any number of biocompatible polymers that are acceptable for short-term blood and tissue contact; examples include silicone, polyurethanes, polysulphones, etc.

The distal end of the lead contains a pin connector for easy connection to a pacing system analyzer/programmer. Generally a 2 mm or 4 mm solid pin is utilized for these applications.

These mapping electrodes are designed for a single procedure and as such would be manufactured from materials and processes that would keep their cost to a minimum. This may include the use of a single solid conductor, non-implantable grade polymer insulation and or simple pin connector.

During a procedure where a minimally invasive remotely steerable lead implant tool is being employed the use of this mapping electrode may eliminate the need for additional surgical instrumentation and reduce procedural time while adding to a successful outcome.

Electrode Impedance Indication

A surgeon placing an epicardial pacing lead that is being placed using mini-thoracotomy techniques is faced with three disadvantages when compared to open surgery.

The visualization of the insertion area is displayed on a 2D monitor that does not provide depth perception.

The use of remote introducer tools reduces or eliminates tactile feedback.

The scope is typically deployed at an angle that does not provide a profile view of the helical fixation electrode.

These factors preclude a surgeon from determining when the helical fixation device has initiated engagement and so precludes counting turns as the sole means to determine proper fixation without over turning.

Figure 21:
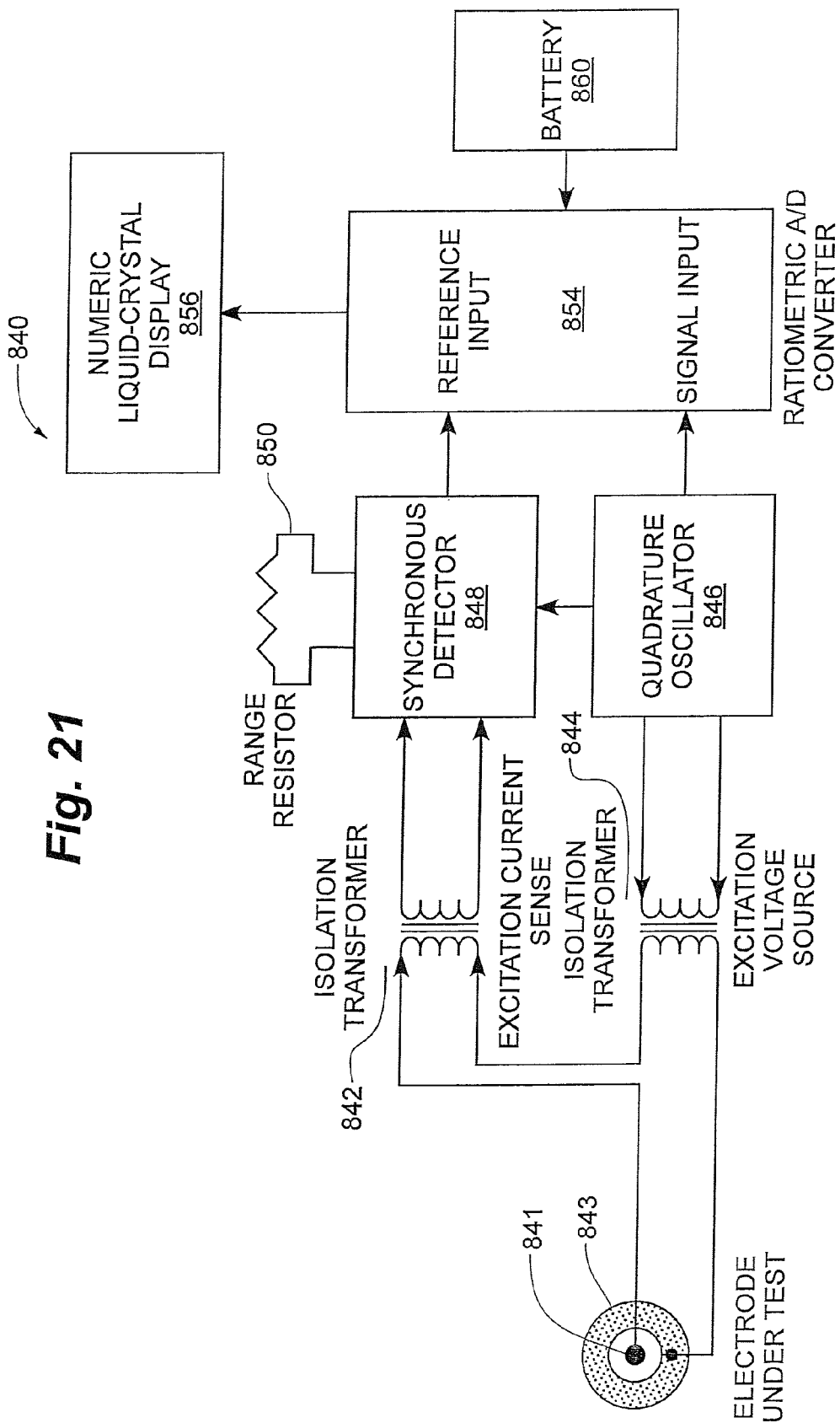
FIG. 21 is a circuit diagram for measuring electrode contact resistance.

FIG. 21 illustrates a circuit 840 that would essentially measure the impedance of the contact between the helical electrode 841 and the ring electrode 843 and the cardiac muscle into which it has been installed. This electrical circuit can be embodied as a low cost circuit that is sold as part of a single use introducer tool or a more refined reusable module that connects to the wire leads of the bipolar electrode.

The electrical circuit measures electrical impedance by applying an AC excitation voltage to the electrode wires and measuring the induced current. Electrical impedance is calculated from the ratio of excitation voltage to induced current. Compared to DC methods, this AC technique offers several benefits. The circuit avoids measurement errors caused by electrolysis and electrode polarization. Also, by using excitation frequencies of 10 kHz or above, it precludes undesired muscular responses. In addition, by observing the phase shift between voltage and current, the impedance measurement can be resolved into reactive and resistive components, corresponding to respective values for capacitance and resistance.

Electrical safety is enhanced several ways. Both the applied excitation voltage and the induced current measurement are transformer isolated by excitation current sense isolation transformer 842 and excitation voltage source 844. There are no electrical energy sources on the isolated side of either transformer. The maximum excitation voltage (corresponding to an open-circuited electrode) and the maximum induced current (short-circuited electrode) are independently limited to safe values by passive failsafe components within the circuit.

The circuit includes a quadrature oscillator 846 with two sine wave outputs. These outputs have a 90° phase difference. When resistance measurements are taken, a single sine wave drives the excitation transformer and the synchronous detector. To make reactance measurements, one sine wave drives the excitation transformer while the other sine wave drives the synchronous detector 848. In addition the quadrature oscillator provides the analog-to-digital converter with a DC voltage input that is proportional to sine wave Amplitude.

The excitation transformer secondary ties an AC voltage to a series-connected circuit consisting of the primary winding of the current-sensing transformer, the pacer leads, and the unknown impedance that terminates the pacer electrodes. The secondary of the current-sensing transformer connects to the input of the synchronous detector. This input is maintained at wound potential by active circuitry within the detector. As a result of this, the primary winding of the current-sense transformer presents zero impedance to the excitation current, and the full excitation voltage a is applied to the pacer leads. This approach allows a direct means of calculating the impedance of the pacer leads and their termination. It is proportional to the ratio of amplitudes of two AC signals on the non-isolated side of the circuit, the quadrature oscillator voltage output and synchronous detector input current.

The synchronous detector 848 demodulates the AC input current and converts it to a proportional DC voltage. The demodulator is driven by one of the sine wave outputs from the quadrature oscillator (selected according to whether a resistance or reactance measurement is being taken). Current-to-voltage scaling within the synchronous detector is set by a range resistor 850, the value of which is determined by the range of actual impedance measurements.

A ratiometric analog-to-digital converter (A/D) 854 can calculate the resistance (or reactance component of the unknown electrode termination impedance. To maximize noise rejection, an integrating A/D is used. The A/D signal-input is the DC output from the quadrature oscillator that proportional to the AC excitation of the unknown electrode termination. The reference-input for the A/D is the DC output from the synchronous detector representing the current induced in the termination.

Digital output from the A/D can be displayed on a low-power liquid-crystal display (LCD). This choice of readout makes battery operation practicable. A single 3-volt lithium cell or a low-cost 9-volt battery 860 could power the entire circuit.

Low-cost product version could eliminate the A/D and LCD. The integrity of electrode placement could be indicated by light-emitting diodes (LED) that flash at a variable rate. A high flash rate could indicate a high impedance condition. A low flash rate, or constant LED illumination, could indicate satisfactory placement of the pacer electrode.

This device can provide a visual indication of when a bipolar lead with helical fixation has been adequately (but not excessively) rotated for installation.

The device above can be used to indicate that a bipolar epicardial pacing lead with a helical fixation device plate/ring pole has been properly installed and has been screwed in adequately but not beyond what is required so as to avoid cardiac tissue damage. Such an indicator would be especially useful during minimally invasive procedures where tactile feedback through steerable remote insertion tools and visualization of the procedure is limited.

Figure 22:
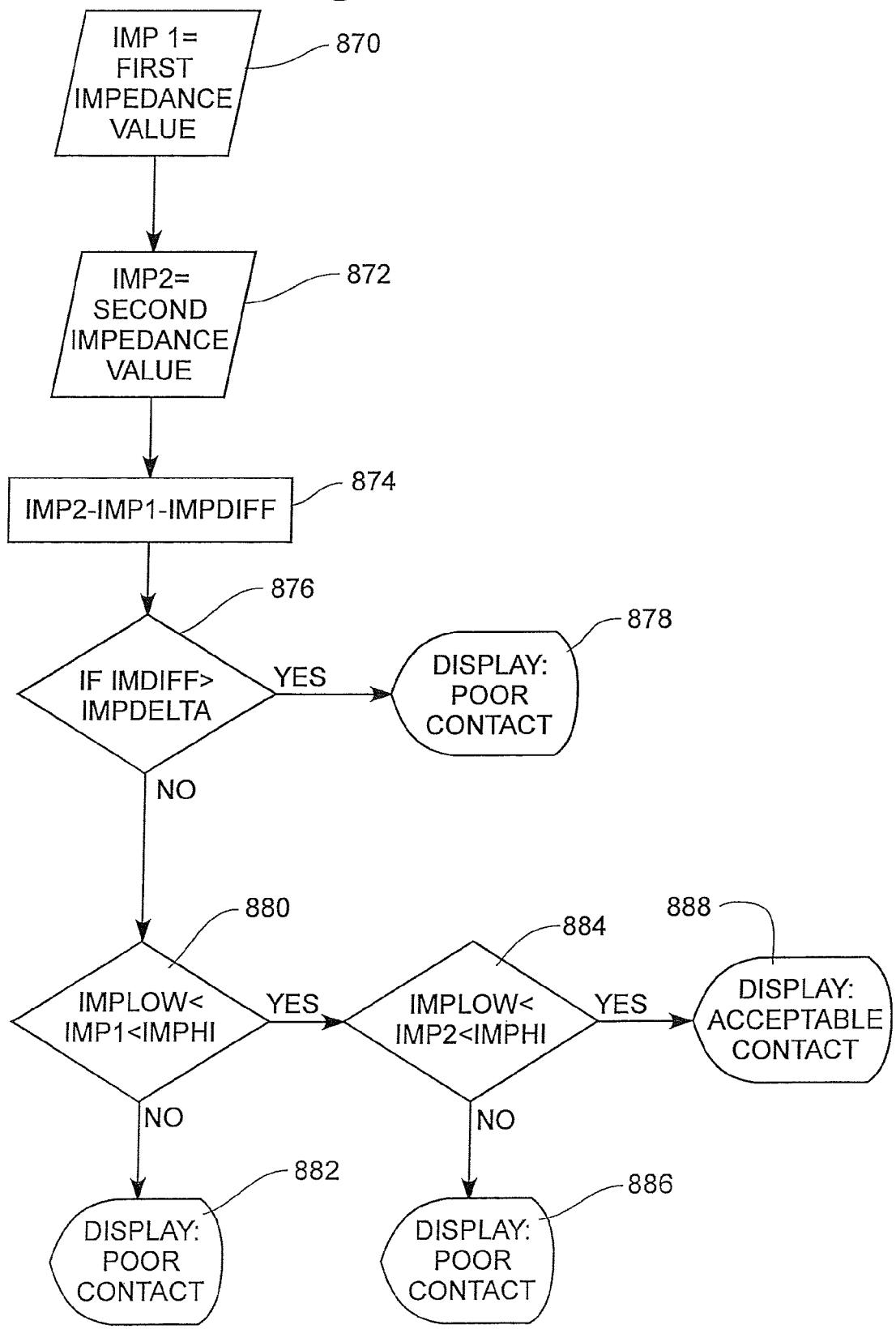
FIG. 22 is a flow chart of a method for outputting an indication of contact quality for a human operator.

FIG. 22 show one algorithm for determining fixation. The steps below may be performed to practice one aspect of the present invention. (1) Place helical fixation point on the selected sight. Rotate two full turns clockwise. (2) Allow the introducer to rest on the myocardium in an unstressed condition. Take a first reading with the indicator circuit (shown at step 860); (3) Apply gentle tension to the introducer in a direction substantially normal to the myocardium. Take a second reading with the indicator circuit (step 872) and take the difference ImpDiff at step 874; (4) Circuit compares the value of the first and second reading to preprogrammed values for impedance and to each other. The value ImpDelta in step 876 can be an empirically predetermined minimum acceptable impedance difference a bipolar electrode contact in a free and tensioned condition. The circuit can determine if proper fixation has been achieved or if additional torquing is required. If the value is too large, poor contact can be indicated at 878.

In step 880, empirically predetermined values ImpLow and ImpHi can be used, for the minimum and maximum acceptable impedance values for a bipolar electrode in free and tensioned condition, respectively. Poor contact can be indicated at 882. At step 884, if Imp2 is between ImpLow and ImpHi, the acceptable contact can be indicated at 888, otherwise poor contact can be indicated at 886.

The lead introducer can be composed of several different types of stainless steel and resins. The handle, outer tube, rod linkage, wheel, release lever and rotation knob can be injection molded from a polycarbonate resin in some embodiments of the invention. ABS or similar rigid-type plastics may be used in some devices. Additionally, the wheel, release lever and rotation knob can be overmolded with a thermoplastic elastomer such as Santoprene (ExxonMobile Chemical) or PeBax (Elf Atochem). This can supply a tactile grip at important user interface sites.

In some devices according to the present invention, the collet can be machined from a 400 series stainless steel that is heat-hardenable. The hardened collet is able to recover from much higher strains and allows for opening/closing during lead head grasping/regrasping. Other components may be made from 300 series stainless steels. The lead release wire may be a cable for improved flexibility and may have a protective coating, for example, a Nylon, which can prevent damage to the filaments. The lower hinge and wedge ring may have a lubricious coating such as Dicronite to facilitate free rotation of the collet during lead implantation.

Some devices according to the present invention are approximately 45 cm from the butt of the handle to the tip of the collet. The shaft length may be approximately 22 cm, with a maximum OD of 14.2 mm in some devices. This particular embodiment OD constraint is to allow insertion through a 15 mm port, which is currently the standard of care. In some devices, the device length is less than about 50 cm, the outer tube has an OD of less than about 15 mm or 25 MM, and the collet jaws have a minimum ID of less than about 0.4 inches.

Mapping electrodes can be made of the similar materials that pacing leads are manufactured from. The external body and head can be made from polyurethane or silicone. The conductor may be made from a stainless steel, MP35N, or a precious metal alloy. Some configurations include solid wire, braided/stranded cable, or coil. Electrodes may be fashioned from platinum or platinum alloy and may have a platinized surface. The pin connectors can be stainless steel or MP35N, and may be fashioned in such a way as to prevent accidental insertion into a pacemaker.

Overall length of some devices can be 35-60 cm, with a body OD of about 0.035 inch to 0.095 inch. The head can mimic the dimensions of current pacing leads, which have an OD of approximately 0.295 inch and a depth of 0.157 inch. The button electrode can protrude approximately 1 mm and the needle electrode approximately 3.5 mm. Some mapping electrodes have an OD of less than about 0.4 inch and a depth of less than about 0.3 inch. Other mapping electrodes have a head OD of about 0.3 inch and a depth of about 0.2 inch.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for inserting an electrode of a lead into a body tissue intended to be stimulated, comprising the steps of:
  a) providing a device comprising: an elongate shaft having a proximal portion and a distal portion; a first distal member pivotally coupled to the elongate shaft distal portion; a second distal member rotatably coupled to the first distal member, wherein the second distal member includes a portion for releasably engaging the electrode; a rotatable tube having a proximal portion and a distal portion, the tube being disposed around the elongate shaft and rotatably flexibly coupled over the first distal member pivotal coupling to the second distal member; a first elongate member having a distal region actuatably coupled to the second distal member portion for releasably engaging the electrode, and having a proximal portion actuable from the shaft proximal portion to release the electrode; and a second elongate member having a distal region operably coupled to the first or the second distal member for causing the first distal member to pivot relative to the elongate shaft, and having a proximal portion actuable from the shaft proximal portion;
  b) manipulating the proximal portion of the first elongate member to cause the distal portion thereof to move the second distal member into releasable engagement with a lead electrode;
  c) advancing the device including the lead through an incision or port in a human body until the lead electrode is proximate the body tissue;
  d) manipulating the proximal portion of the second elongate member to pivot the first distal member rotatably coupled to the second distal member relative to the shaft to thereby orient the second distal member and the lead electrode into a position for securing the electrode to the body tissue;

e) manipulating the rotatable tube to thereby rotate the first distal member rotatably coupled to the second distal member releasably engaged with the lead electrode to thereby cause the electrode to screw into the body tissue;

f) further manipulating the proximal portion of the first elongate member to cause the second distal member to release from the lead electrode; and g) removing the device from the incision or body port.

2. The method of claim 1 including providing the elongate shaft as a tube having the first and second elongate members disposed within.

3. The method of claim 1 including providing the first and second elongate members being slidably disposed within the elongate shaft.

4. The method of claim 1 including providing the second elongate member operably coupled to the first or second distal member forming a lever arm with respect to the pivotal coupling of the elongate shaft to the first distal member.

5. The method of claim 1 including actuating the second elongate member in both compression and in tension.

6. The method of claim 1 including moving the release engagement portion in a reversibly transversely direction relative to a central longitudinal axis of the shaft to urge the second distal member in a transversely outwardly direction to release the lead electrode.

7. The method of claim 6 including providing the second distal member comprising a collet having jaws, and providing the first elongate member being operably coupled to an element for urging the jaws apart when the first elongate member is proximally retracted.

8. The method of claim 7 including manipulating the first elongate member to release a caroming force on the jaws, thereby allowing the jaws to open when the first elongate member is proximally retracted.

9. The method of claim 1 including providing the first elongate member acting only in tension.

10. The method of claim 1 including providing the second elongate member being operably coupled to the second distal member.

11. The method of claim 1 including coupling a manually operable rotatable portion to the tube, the manually rotatable portion having a larger radius then the tube and being coupled to effect rotation of the tube.

12. The method of claim 1 including actuating the first elongate member proximal portion through a slider element.

13. The method of claim 1 including providing at least one guide along an external surface of the tube to secure the lead to the tube.

14. The method of claim 13 including manipulating the lead body axially within the guide.

15. The method of claim 1 including providing the first distal member being a distal portion of a hinge with the second distal member including a collet rotatably disposed about the hinge distal portion.

16. The method of claim 1 including providing the second distal member including a collet comprising jaws that can be urged apart through a camming action actuated from the device proximal portion using the first elongate member.

17. The method of claim 1 including inserting either an epicardial-myocardial cardiac lead having a helical electrode or, a mapping lead comprising an electrode having either a dull shape or a straight needle shape.

18. A method for inserting an electrode of a lead into body tissue to be stimulated, comprising the steps of:

a) providing a device comprising: an elongate shaft having a proximal portion and a distal portion; a hinge having a proximal portion coupled to the elongate shaft distal portion, and a distal portion; a lead grasping member rotatably coupled to the hinge distal portion and including jaws configured and dimensioned to releasably grasp the lead, and an internal camming surface of the jaws; a camming element disposed within the lead grasping member and biased to apply force to the camming surface to open the jaws; a first elongate member having a distal region coupled to the camming element to reduce the bias when the first elongate member is proximally retracted, and a proximal portion actuatable from the device proximal portion; a second elongate element having a distal region operably coupled to the hinge distal portion and a proximal region actuatable from the device proximal portion; and a tube rotatably disposed over the elongate shaft and rotatably coupled to the lead grasping member over the hinge;

b) manipulating the proximal portion of the first elongate member to cause the distal portion thereof to cause the camming element disposed within the lead grasping element to apply a biasing force against the camming surface to open the jaws and then further manipulating the first elongate member to reduce the biasing force of the camming element against the camming surface to close the jaws on the lead electrode;

c) advancing the device including the lead through an incision or port in a human body until the lead electrode is proximate the body tissue;

d) manipulating the proximal portion of the second elongate member to pivot the hinge relative to the shaft to thereby orient the lead grasping member and the lead electrode into a position for securing the electrode to the body tissue;

e) manipulating the rotatable tube to thereby rotate the lead grasping element releasably engaged with the lead electrode relative to the shaft to thereby cause the electrode to screw into the body tissue;

f) further manipulating the proximal portion of the first elongate member to increase the biasing force of the camming element against the camming surface of the lead grasping member to thereby open the jaws and release the lead electrode from the lead grasping member; and g) removing the device from the incision or body port.

19. The method of claim 18 including providing the lead grasping member as a collet having teeth disposed about a periphery of the electrode.

20. The method of claim 19 including providing the lead grasping member having an inter-tooth spacing of no greater than about 100 degrees.

21. The method of claim 18 including providing the camming element as a Belleville washer.

22. The method of claim 18 including providing at least one guide for holding the lead along the rotatable tube while the tube is rotating.

23. The method of claim 18 including inserting either an epicardial-myocardial cardiac lead having a helical electrode or, a mapping lead comprising an electrode having either a dull shape or a straight needle shape.

* * * * *